United States Patent
Bauer et al.

(10) Patent No.: US 10,669,350 B2
(45) Date of Patent: Jun. 2, 2020

(54) ANTIGEN-BINDING CONSTRUCTS THAT BIND TO AND INHIBIT CATALASE AND/OR SUPEROXIDE DISMUTASE AS WELL AS PHARMACEUTICAL COMPOSITIONS CONTAINING THEM FOR TUMOR THERAPY

(71) Applicants: Georg Bauer, Freiburg (DE); Manfred Motz, Munich (DE)

(72) Inventors: Georg Bauer, Freiburg (DE); Manfred Motz, Munich (DE)

( * ) Notice: Subject to any disclaimer, the term of this patent is extended or adjusted under 35 U.S.C. 154(b) by 0 days.

(21) Appl. No.: 15/543,215

(22) PCT Filed: Feb. 1, 2016

(86) PCT No.: PCT/EP2016/052016
§ 371 (c)(1),
(2) Date: Jul. 12, 2017

(87) PCT Pub. No.: WO2016/124512
PCT Pub. Date: Aug. 11, 2016

(65) Prior Publication Data
US 2018/0002445 A1    Jan. 4, 2018

(30) Foreign Application Priority Data
Feb. 2, 2015 (EP) ............................. 15153421

(51) Int. Cl.
| | | |
|---|---|---|
| *C07K 16/40* | (2006.01) | |
| *C07K 16/30* | (2006.01) | |
| *A61K 31/337* | (2006.01) | |
| *A61K 39/395* | (2006.01) | |
| *A61K 45/06* | (2006.01) | |
| *A61K 39/00* | (2006.01) | |

(52) U.S. Cl.
CPC ............ *C07K 16/40* (2013.01); *A61K 31/337* (2013.01); *A61K 39/39558* (2013.01); *A61K 45/06* (2013.01); *C07K 16/3046* (2013.01); *A61K 2039/505* (2013.01); *A61K 2039/507* (2013.01); *C07K 2317/22* (2013.01); *C07K 2317/31* (2013.01); *C07K 2317/55* (2013.01); *C07K 2317/565* (2013.01); *C07K 2317/569* (2013.01); *C07K 2317/73* (2013.01); *C07K 2317/76* (2013.01)

(58) Field of Classification Search
CPC ........................ C07K 16/40; A61K 39/39558
USPC ...................................................... 424/136.1
See application file for complete search history.

(56) References Cited

U.S. PATENT DOCUMENTS 9,862,777 B2 * 1/2018 Robberecht ............ C07K 16/40

FOREIGN PATENT DOCUMENTS

| EP | 2 679 225 | 6/2012 |
| EP | 2 535 352 | 12/2012 |
| WO | WO 2014/191493 | 12/2014 |

OTHER PUBLICATIONS

Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Huang et al. (Appl Microbiol Biotechnol (2010) 87:401-410)).*
Bauer et al. (Anticancer Research 36: 5945-5956 (2016)).*
Abeijon et al. (Parasite Immunol. Nov. 2018;40(11):e12584. doi: 10.1111/pim.12584. Epub Sep. 11, 2018).*

* cited by examiner

*Primary Examiner* — Lynn A Bristol
(74) *Attorney, Agent, or Firm* — Chalin A. Smith; Smith Patent, LLC

(57) ABSTRACT

The invention relates to single domain VHH fragments which specifically bind to and inhibit superoxide dismutase and/or bind to and inhibit catalase and/or bind to and inhibit superoxide dismutase and catalase, in particular for the use in the therapy of tumor diseases.

10 Claims, 27 Drawing Sheets
Specification includes a Sequence Listing.

Scheme 1

Scheme 2

Scheme 3

Scheme 4

Scheme 5

Scheme 6

Scheme 7

Scheme 8

Scheme 9

Scheme 10

Scheme 11

Scheme 12

ANTIGEN-BINDING CONSTRUCTS THAT BIND TO AND INHIBIT CATALASE AND/OR SUPEROXIDE DISMUTASE AS WELL AS PHARMACEUTICAL COMPOSITIONS CONTAINING THEM FOR TUMOR THERAPY

PRIORITY

This application corresponds to the U.S. national phase of International Application No. PCT/EP2016/052016, filed Feb. 1, 2016, which, in turn, claims priority to European Patent Application No. 15.153421.1 filed Feb. 2, 2015, the contents of which are incorporated by reference herein in their entirety.

SEQUENCE LISTING

The instant application contains a Sequence Listing that has been submitted in ASCII format via EFS-Web and is hereby incorporated by reference in its entirety. Said ASCII copy, created on Jul. 12, 2017, is named LNK_184US_SequenceListing_English.txt and is 21,494 bytes in size.

FIELD OF THE INVENTION

The present invention is based on the unexpected finding that antigen-binding constructs, in particular single domain VHH fragments (nanobodies) either neutralizing human catalase or human SOD1 cause a more than a hundred times greater efficiency in the reactivation of intracellular ROS forced signal paths that results in tumor apoptosis than the classical recombinantly produced Fab fragments or monoclonal antibodies both consisting of a light and heavy chain proportion that both also exhibit neutralizing effect on catalase or SOD1, respectively. The application of single domain VHH fragments against catalase or SOD reactivates intercellular ROS signaling and leads to the apoptosis of the cells. Single domain VHH fragments against one of the two protective enzymes are sufficient to eliminate the protection of the tumor cells from ROS signaling, even though the protective effect of catalase and SOD partially is redundant and interrelated. This is based on the fact that SOD achieves only a partial protective effect, but the inhibition of the SOD results in an indirect inhibition of the catalase by the superoxide anions that are now present in an increased concentration. The quality of the signal paths caused by the inhibition of SOD or catalase is different. The inhibition of catalase permits the sequential activation of the NO/peroxynitrite and HOCl path, whereas the inhibition of the SOD exclusively results in the reactivation of the NO/peroxynitrite path. Of high therapeutic importance is the finding that single domain VHH fragments against SOD and catalase cooperate synergistically and that said synergy effect in a preferred embodiment can be concentrated in a hybrid molecule. On this basis, there is disclosed an advantageous form of therapy of tumors with antigen-binding constructs that bind to SOD or catalase or both antigens.

BACKGROUND OF THE PRESENT INVENTION

It was found only a few years ago that reactive oxygen and nitrogen species (together abbreviated as reactive oxygen species="ROS") in addition to their non-directional mutagenic effect can also exert specific signal functions (Bauer et al., Chimica, 62, 1-9, 2008). The perception of said finding was especially complicated by the fact that by certain ROS quite often opposite biological effects can be caused.

EP 11170076.1 discloses that the inhibition of the protective membranous catalase of tumor cells results in a reactivation of the intracellular ROS signaling and thus, to the selective cell death of tumor cells. An inhibition of the protective catalase can also be achieved indirectly by the inhibition of a membranous SOD, since after the inhibition of the SOD the superoxide anions generated by the adjacent also membranous NADPH oxidase are no longer converted to $H_2O_2$. In this way, now there is present a sufficiently high local concentration of free superoxide anions that convert the active intermediate Compound I of the catalase ($CATFe^{IV}=O.^+$) to the inactive intermediate Compound II ($CATFe^{IV}=O$) via a one-electron transfer and additionally convert active catalase ($CATFe^{III}$) to the inactive Compound III ($CATFe^{III}O_2$). By these two reactions the activity of the catalase is effectively inhibited (Kono Y and Fridovich I: Superoxide radical inhibits catalase. J Biol Chem 257:5751-5754, 1982. Shimizu N, Kobayashi K and Hayashi K: The reaction of superoxide radical with catalase. Mechanism of the inhibition of catalase by superoxide radical. J Biol Chem 259: 4414-4418, 1984).

However, for the role of ROS in the multi-stage oncogenesis nowadays a fairly clear picture can be drawn, the knowledge of which could show the way forward to the establishment of new selective tumor therapy methods (summarized in Bauer G. Tumor cell protective catalase as a novel target for rational therapeutic approaches based on specific intercellular ROS signaling. Anticancer Res. 32: 2599-2624, 2012; Bauer G. Targeting extracellular ROS signaling of tumor cells. Anticancer Res. 34: 1467-1482, 2014; Bauer G. Increasing the endogenous NO level causes catalase inactivation and reactivation of intercellular apoptosis signaling specifically in tumor cells. Redox Biol. 6: 353-371. 2015):

1) The mutagenic effect of ROS contributes to the classical step of "tumor initiation".
2) ROS are of crucial importance for the step of "tumor promotion", without the underlying mechanism being explained in detail. So, most of the known tumor promoters induce increased ROS levels and the specific scavenging of ROS inhibits the effect of most of the tumor promoters.
3) The malign transformation of cells regularly results in the expression of a membranous NADPH oxidase (NOX1). The continuous activity of this enzyme is of essential importance both for the proliferation of the malign cells and for maintaining the transformed state. NOX1 generates extracellular superoxide anions the dismutation product of which, $H_2O_2$, represents an autocrine proliferation stimulator for the cells.
4) However, the generation of extracellular superoxide anions also represents the basis for the formation of intracellular ROS controlled signal paths that selectively induce apoptosis of the transformed cells. Here, the "HOCl signal path" and the "NO/peroxynitrite signal path" that are explained in detail below are of particular importance.
   Thus, the specific ROS dependent apoptosis induction in transformed cells is discussed as a potential elimination mechanism for malign cells.
5) A successful development of tumors requires that ROS producing malign cells protect themselves from the destructive effect of the ROS signal paths without thereby affecting the autocrine ROS production that is necessary for their proliferation. This results in the phenotype of tumor cells that is found regularly and in all tumor systems studied so far and that is characterized by a constitutive NOX1 activity and parallel activity of a membranous catalase. Additionally, a further modulation of the ROS signaling by membranous superoxide dismutase (SOD) takes place.

6) The selective inhibition of these membranous protective enzymes permits a ROS dependent selective apoptosis induction in tumor cells and thus, has great therapeutic potential.

SUMMARY OF THE INVENTION

Considering the mechanisms briefly outlined above and further explained below that in general are quite complex and difficult to predict due to the interactions the present invention discloses antigen-binding constructs, in a broad meaning, that can be used in particular for tumor therapy. Thus, the object of the present invention are antigen-binding constructs, namely single domain VHH fragments, also called nanobodies, which specifically bind to and preferably inhibit either superoxide dismutase or catalase or both enzymes, namely superoxide dismutase and catalase.

WO 2014/191493 discloses single domain antibodies against SOD1 and their use in the treatment of ALS (amyotrophic lateral sclerosis). Here, the level of pathogenic SOD1 in patients suffering from ALS is to be reduced by single domain antibodies directed against SOD1 to achieve a positive effect.

The antigen-binding constructs according to the invention are single domain VHH fragments against catalase or SOD. Here, the same apoptosis causing effect is achieved with less than one percent of the concentration of comparable conventional Fab fragments, even though due to the different structure of the VHH and Fab fragments (one versus two chains) a concentration difference of only 50% would have been expected. This dramatic difference in the efficacy was found for all catalase- or SOD-neutralizing single domain VHH fragments and thus, represents their characteristic feature. This indicates that there must be a so far not recognized and also not predictable basic difference with far-reaching consequences for the effect of the fragments and thus, also for their very much improved therapeutic possibilities of employment between the kinetics of the bond and the reversibility of the bond for conventional Fab fragments and single domain VHH fragments. As a basis for explaining this discovery there can be used the difference between the identification of epitopes by classical Fab fragments (consisting of antigen-binding proportions of the heavy and light chain of the immunoglobulin molecule) and by VHH fragments of the single domain antibodies (that only consist of the antigen-binding proportion of heavy chains). While classical Fab fragments bind to a specific epitope, and to certain extent include it, wherein the bond is defined by the spatial structure and the surface charge of the Fab fragments, single domain VHH fragments have a plug-shaped structure that fits into a recess of the target molecule that is complementary with respect to shape and charge (Muyldermans S. Nanobodies: Natural single domain antibodies. Ann. Rev. Biochem. 82: 775-797, 2013). It is assumed that the single domain VHH fragments disclosed in this application that effectively inhibit either catalase or SOD bind into the funnel that is characteristic for these enzymes and passes the substrate molecules to the active center. It is conceivable that after such a binding a change in conformation of the enzymes is induced that effectively prevents the reverse reaction, i.e. the termination of the bond between the single domain VHH fragment and the antigen. In this way, the biophysical parameter "affinity" that is determined by the reaction constants of the direct and reverse reaction is substantially increased since no reverse reaction takes place. In practice, in this way a much more efficient neutralizing effect by single domain VHH fragments is achieved than conventional Fab fragments can achieve this, even if their binding should take place with the same efficiency. This essential advantage of single domain VHH fragments in the inhibition of specific enzymes has not yet been described and is surprising.

It cannot be ruled out that certain single domain VHH fragments achieve their inhibiting effect on catalase or SOD by the fact that their binding takes place to a position in the enzyme that is different from the active center, but in this way by the known allosteric distant effects within a protein an inhibiting effect on the enzyme activity is achieved. Due to the results according to the invention also for this variation of the chain of effects it can be assumed that the affinity of the single domain VHH fragments for the region on the enzymes causing the allosteric inhibition must be significantly higher than it can be achieved by classical Fab fragments. Thus, the invention is not limited to single domain VHH fragments that directly bind to the active center of the enzyme.

As to the structure of artificially produced antibody fragments it should be noted that meanwhile there is an enormous variety of different structures. In the article of Holliger et al. (2005), Nature Biotechnology, Vol. 23, No. 9, pages 1126-1136 there are illustrated and explained various structures of antigen-binding molecules. In addition to the VHH single domain fragments used in accordance with the invention there are also many other structures such as Fab fragments, single chain $F_v$, diabodies, minibodies, triabodies, and other.

The single domain antibody fragments used in accordance with the invention are derived from antibody molecules of camelidae (camel, llama, alpaca). These antibodies in the natural phenotype have an Fc part (with CH2 and CH3), but consist of two heavy chains that each in turn have a VHH part with the CDRs. Light chains do not have these antibodies of the camelidae. These VHH parts are referred to as single domain VHH fragments or also nanobodies.

The single domain VHH fragments according to the invention either can be used as such or can also be modified chemically to achieve certain aims. The single domain VHH fragments according to the invention either by covalent chemical bond or by other chemical interactions such as ionic interactions or van der Waals forces can be connected to other components that have an advantageous effect. These may be conjugates with biologically active molecules such as ligands and/or receptors that can bind to specific cells. It is also possible that the single domain VHH fragments according to the invention are linked to imaging materials such as radionuclides, color-producing enzymes, and the like. The molecules according to the invention may also be connected to molecules that result in a prolonged retention time in the body; this can be effected for example by connecting them to larger polymers such as for example polyethylene glycol. Various possible employment options and modifications of the single domain VHH fragments are disclosed in the review article of Eyer et al., Veterinarni Medicina (2012), 9, pages 439-531. Reference is explicitly made to this bibliography.

In a further preferred embodiment there are represented hybrid molecules that "in themselves concentrate" the synergy effect, although due to the structure it can be excluded that one and the same hybrid molecule at the same time binds to catalase and SOD. This sets apart the effect of these hybrid molecules from the classical bi-specific antibodies that generally have to bind to both target structures to achieve the intended effect.

A substantial aspect of the present invention is that the antigen-binding constructs do not only specifically bind to the respective target molecules (superoxide dismutase and catalase), but also inhibit them. Said aspect is tested by standard methods that are well known to the skilled person. In a suitable test model, for example tumor cells that express the desired target molecule (catalase or superoxide dismutase) on the cell surface or in a test system, to which purified SOD or catalase was added, the substrates for the respective enzymes are added or produced by the cells. Then, either the consumption of the educts or the generation of the products is measured by suitable measuring methods. Here, there can also be applied methods in which a biological process such as for example induction of the ROS dependent apoptosis of tumor cells is employed as a parameter. A prerequisite for the meaningfulness of said generally quite sensitive biological method is that the substrate degraded by the enzyme to be tested is in a controllable and quantitative context with the measured biological effect. This is especially the case for SOD and catalase. For example, SOD metabolizes the superoxide anions required for the intracellular ROS signaling to $H_2O_2$ and thus, prevents the interaction between superoxide anions and HOCl that is required for the HOCl dependent apoptosis induction.

Thus, the inhibition of the SOD mediated by single domain VHH or Fab fragments (comparison) can be determined by the fact that the apoptosis induction of tumor cells by exogenously added HOCl is employed as the test system. HOCl in a concentration depending manner induces apoptosis that is based on the interaction between HOCl and superoxide anions that results in the formation of aggressive hydroxyl radicals (Bauer G. HOCl-dependent singlet oxygen and hydroxyl radical generation modulate and induce apoptosis of malignant cells. Anticancer Res 33: 3589-3602, 2013). Said apoptosis induction is completely inhibited by SOD that is exogenously added in suitable concentration. That is, the neutralizing effect of single domain VHH or Fab fragments can be determined by checking whether the inhibition of the apoptosis is abolished again by the single domain VHH or Fab fragments to be tested. The quantitative employment of said test system requires linking several simple steps the skilled person is familiar with. In the first step the concentration of commercially available HOCl (or sodium hypochlorite that sufficiently forms HOCl in medium) is determined that generates a significant quantifiable apoptosis signal within a reasonable trial time (1-2 hours). As experience shows, HOCl concentrations between 0.1 and 1 mM are well suited. A parameter is suitably the percentage of apoptotic cells (directly determined by phase contrast microscopy) or the (3-(4,5-dimethylthiazol-2-yl)-2,5-diphenyltetrazoliumbromide (MTT) test that is commercially available and determines the cell viability by measuring the mitochondrial metabolic activity. In a second step, the concentration of SOD is determined that is just sufficient to completely inhibit the effect of the selected concentration of HOCl. As experience shows, for that a SOD concentration between 5 and 50 U/ml is suitable. The accuracy of said determination is of particular importance because the inhibition of the HOCl effect by Cu/Zn-SOD represents itself as an optimum curve and achieving the optimum inhibiting effect is essential for the meaningfulness of the test. As soon as the first two steps have been satisfactorily performed there can take place the actual test of the inhibiting effect of the single domain VHH or Fab fragments. For that, selected concentrations of the fragments to be tested are pre-incubated for 20 minutes with the optimal concentration of SOD determined in advance in step #2. Subsequently, said mixture is added to the test cells. Thereafter, HOCl is added and the apoptosis induction is determined. An optimum inhibition of SOD and thus, a clear result for a neutralizing effect is obtained if the inhibiting effect of SOD was abolished by at least 90%, i.e. an apoptosis induction is achieved that is by only 10% lower than the apoptosis induction without added SOD. If there is achieved an inhibiting effect on SOD that is characterized in that at least 50% of the apoptosis induction of the comparative value without SOD are achieved there is a significant inhibition of SOD. The meaning of such a finding can be further examined by increasing the single domain VHH or Fab fragment concentration in a subsequent trial, since in case of a significant inhibition of SOD with an increase in concentration of the single domain VHH or Fab fragment an increase in the restoration of the apoptosis induction is to be expected.

For the determination of the neutralizing effect of single domain VHH or Fab fragments directed against catalase a test system is suitable that is based on the apoptosis-inducing effect of $H_2O_2$ and the degradation of $H_2O_2$ by catalase. Here, as the cellular test system both non-malignant and malignant cells can be employed. It is only required that apoptosis induction is quantitatively determinable in the selected cell system. As the $H_2O_2$ source, $H_2O_2$-generating glucose oxidase (GOX) is preferred over the direct addition of $H_2O_2$, because the continuous production of $H_2O_2$ by GOX (by using glucose from the culture medium of the cells) allows a very precise adjustment of the $H_2O_2$ flux. The test system is based on the inhibition of the apoptosis induction by GOX mediated by catalase and the restoration of the apoptosis induction by catalase-neutralizing single domain VHH or Fab fragments. In a first step, the concentration of GOX is determined that significantly inhibits apoptosis within an appropriate time (1-2 hours). For that, in general depending on the cell system, GOX concentrations between 0.1 and 40 mU/ml are required. In a second step, the concentration of human catalase is determined that is just sufficient to abolish the effect achieved by GOX. As experience shows, the concentration range required for that is in the range of less than 20 U/ml of catalase. After successful determination of the suitable concentrations of GOX and catalase then the actual experiment for the determination of the catalase-neutralizing effect of single domain VHH or Fab fragments can be performed. For that, the selected catalase concentration is pre-incubated for 20 minutes with selected concentrations of the single domain VHH or Fab fragments to be tested. Subsequently, said mixture together with the concentration of GOX determined to be suitable is added to the cells and apoptosis induction is measured. A reliable neutralizing effect of the single domain VHH or Fab fragments is obtained if the inhibiting effect of the catalase on the GOX-mediated apoptosis induction was abolished by at least 90%, i.e. if 90% of the apoptosis induction value is achieved that is shown in control preparations without addition of catalase. If there is achieved an abolition of the inhibiting effect of catalase of at least 50% there may be assumed a significant inhibiting effect of the tested single domain VHH or Fab fragment. By increasing the concentration of said fragment in subsequent trials a further examination of this finding can be achieved.

As a control in the test methods listed here antigen-binding constructs binding to a completely different antigen are employed. Then, in the actual test, as described above in detail, the constructs each to be investigated are added to the reaction mixture and it is measured whether the enzymatic activity of the catalase or superoxide dismutase is inhibited or not inhibited. For this purpose, various test models can be used the person of average skill in the art is readily familiar with. This finding is important to be able to determine in which way the antigen-binding construct binds to the target enzyme (catalase or SOD, respectively).

It is assumed that in most cases in which the antigen-binding construct does not bind to the catalytic center or in its vicinity the enzymatic activity is not or not substantially inhibited. However, if the antigen-binding construct directly binds to the catalytic center or in its steric vicinity, or despite binding far away from the catalytic center does change the conformation of the target enzyme via an allosteric effect such that the normal reaction of the enzyme can no longer freely take its course, the reactants can no longer react with the enzyme and the conversion can no longer freely take place. Since the determination of absolute values in biochemical systems always varies such tests are preferably carried out in one test preparation, wherein cells in the same state and in the same amount are subjected to different test conditions to be able to make a statement. In the meaning of the present invention an inhibition of the superoxide dismutase and/or catalase is obtained if the catalytic activity of the respective enzyme (or the overall activity of the respective enzyme population) is reduced by at least 50%, preferably by at least 70%, and particularly preferably by at least 90% by the addition of a suitable amount of the antigen-binding construct.

In a further embodiment of the present invention there are provided antigen-binding constructs, preferably nanobodies, that bind to catalase and/or superoxide dismutase and that do not or only partially inhibit these enzymes. Also, these antigen-binding constructs can advantageously be used, said constructs for example being configured such that they can be connected to or are connected to a component serving as a marker. In this way, for example tumor cells can be marked if this is a marker that provides a corresponding signal in a suitable detection system. Alternatively, these constructs can also be connected to a cytotoxic agent or configured such that they can be connected to said cytotoxic agent or optionally connect itself to said cytotoxic effector within the target organism.

In a further preferred embodiment there are used mixtures, wherein some antigen-binding constructs inhibit catalase and/or superoxide dismutase and other constructs do not or only partially inhibit superoxide dismutase and/or catalase. These can also be hybrid molecules that contain two different antigen-binding constructs.

The antigen-binding single domain VHH fragments according to the invention are preferably produced by genetic engineering and do not have an $F_C$ part like complete antibodies. They differ from classical Fab fragments by the lack of light chains. That is, they are only the antigen-binding parts of the heavy chain of an antibody.

BRIEF DESCRIPTION OF THE FIGURES

The following diagrammatic representations first unite the apoptosis-inducing ROS signal paths in transformed cells (scheme 1: HOCl path; scheme 2: NO/peroxynitrite path) and then, show the tumor cell-specific effect of membranous catalase and SOD on these signal paths (Scheme 3 and 4).

In the following diagrammatic representations 5 (FIG. 5) and 6 (FIG. 6) there are summarized the enzymatic details that are required for the understanding of the multiple effect of the protective enzymes catalase and SOD.

Figure 5:
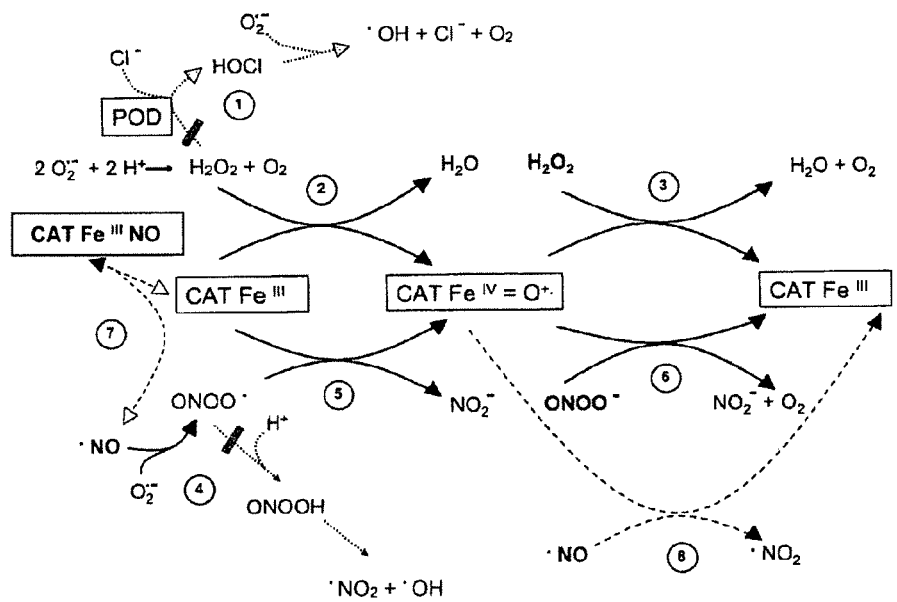

FIG. 5: Scheme 5 shows that the inhibition of the HOCl signal path ① by catalase is effected by a two-stage mechanism ②, ③ in which the catalase intermediate "Compound I" ($CATFe^{IV}=O^+$) is of central importance and is re-formed to native enzyme. On the one hand, the inhibition of the NO/peroxynitrite path ④ takes place by degradation of peroxynitrite via a two-stage mechanism with the participation of Compound I, on the other hand by oxidation of NO ⑧. Oxidation of NO is in an equilibrium with an NO-dependent inhibition of catalase, however that only takes effect at relatively high NO concentrations.

Figure 6:
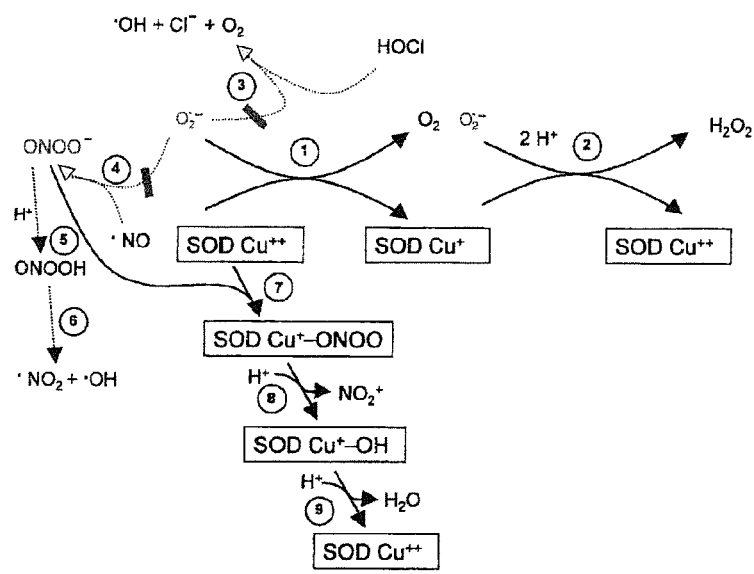

FIG. 6: Scheme 6 shows that the SOD-mediated dismutation of superoxide anions to $H_2O_2$ ①, ② is effected by a two-stage mechanism in which the reduction of the enzyme-bound $Cu^{++}$ and oxidation of the $Cu^+$ play a key role. The reaction of superoxide anions counteracts both the interaction between HOCl and superoxide anions ③ that is essential for the HOCl path and the formation of peroxynitrite ④. Also, SOD has the potential to destroy peroxynitrite via reaction steps ⑦-⑨.

Schemes 5 and 6 show that catalase and SOD, contrary to the textbook knowledge, are not characterized by highly selective reactions, but rather can execute multiple, partially overlapping functions. Altogether, this results in an outstanding plastic and complex biological effect.

Figure 7:
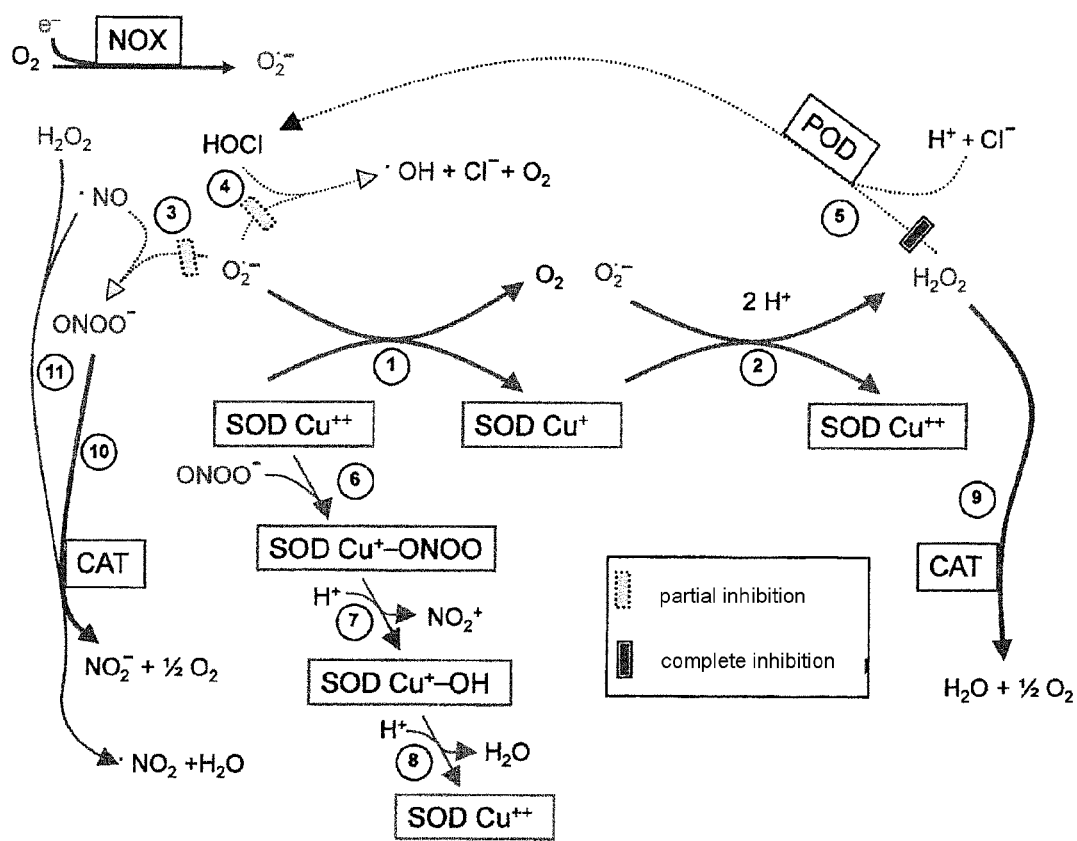

FIG. 7: Scheme 7 represents the overall context between the enzymes acting on the outside of tumor cells. Membranous NADPH oxidase (NOX) generates the superoxide anions that are essential for both signal paths. Membranous SOD converts a substantial part of the superoxide anions to $H_2O_2$ ①, ②. This results in a partial inhibition of the formation of peroxynitrite a and to the partial inhibition of the interaction between superoxide anions and HOCl ④, wherein HOCl was formed by peroxidase (POD) ⑤. Additionally, SOD also decomposes peroxynitrite (sequence of reactions ⑥-⑧). Catalase prevents HOCl synthesis by degradation of $H_2O_2$ ⑨, degrades peroxynitrite ⑩ and prevents the formation of peroxynitrite by oxidation of NO ⑪.

Figure 8:
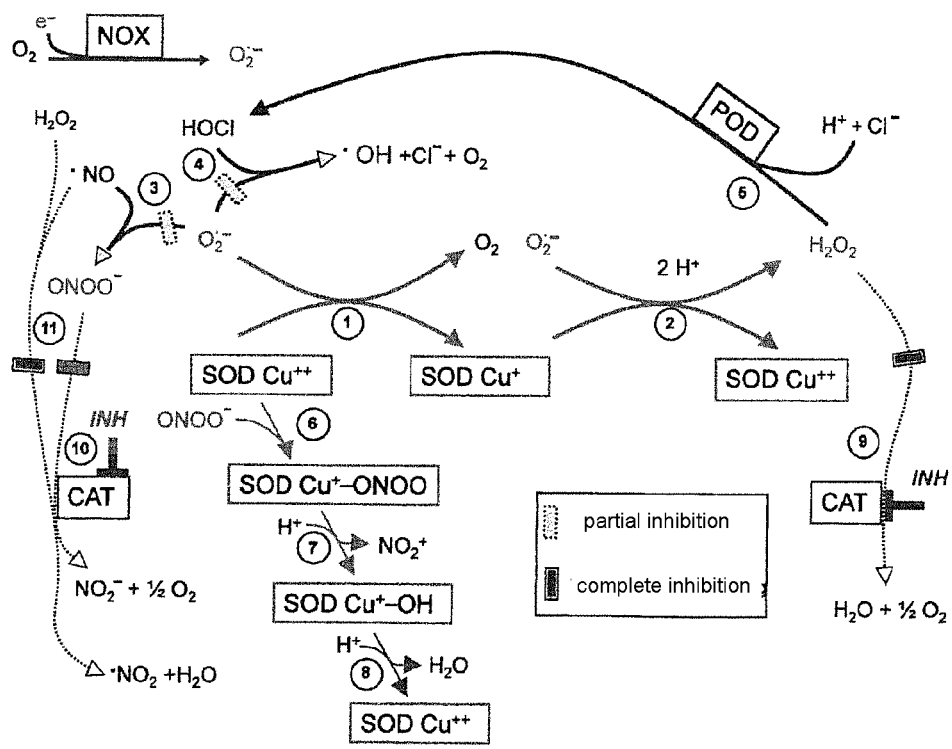

FIG. 8: Scheme 8 is a diagrammatic representation of the conclusion that results from the facts summarized in Scheme 7, wherein a sole inhibition of membranous catalase ⑨, ⑩ can result in a reactivation of the HOCl signal path and the NO/peroxynitrite path, since SOD only achieves a partial protection of steps ③ and ④.

Figure 9:
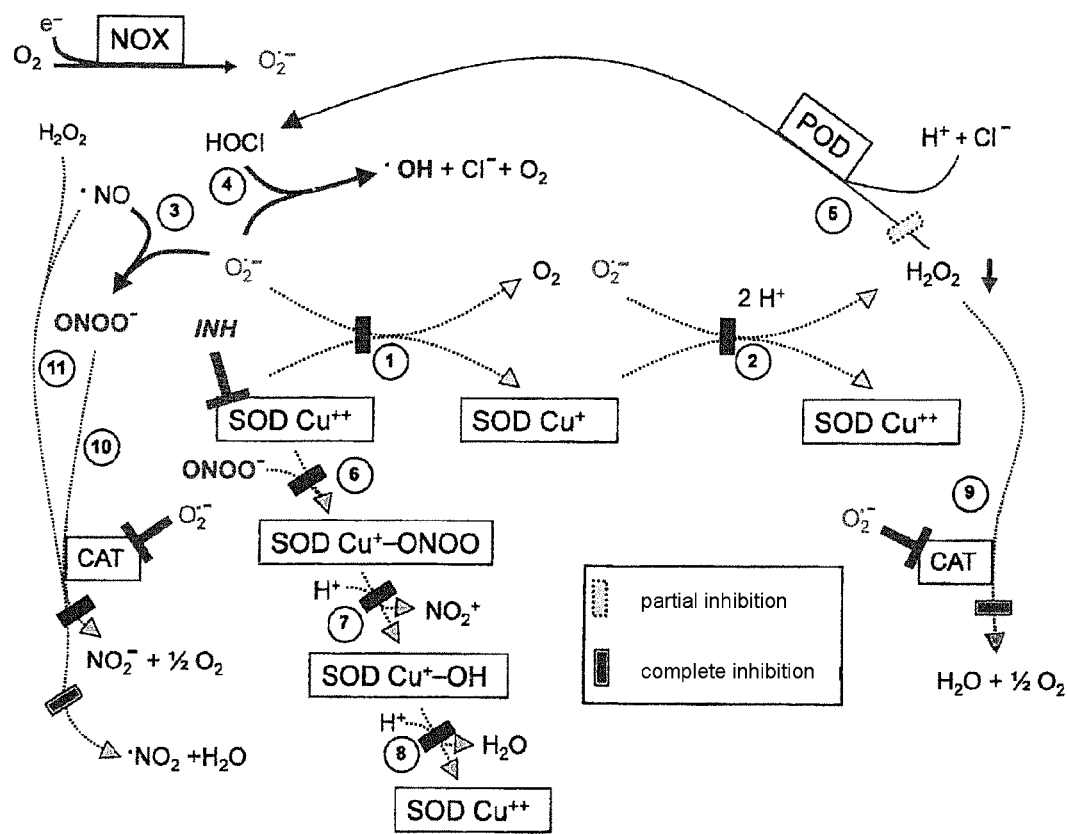

FIG. 9: Scheme 9 demonstrates that the assumption that an inhibition of SOD would not be sufficient for a reactivation of the apoptosis-inducing signal paths, since the dominant inhibiting effect of catalase should be opposed thereto, is incorrect. The key for the understanding of this initially unexpected finding is the inhibiting effect of superoxide anions on catalase. Since after the inhibition of SOD a local increase of the concentration of superoxide anions is observed (that is only counteracted by the spontaneous dismutation reaction) an indirect inhibiting effect on the catalase is achieved if SOD was only inhibited directly.

Figure 10:
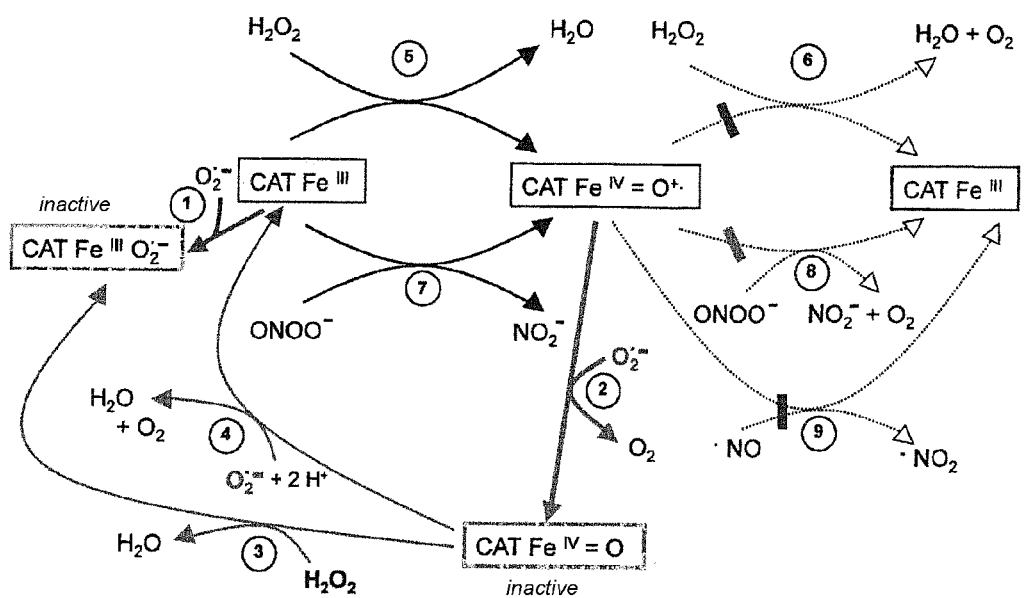

FIG. 10: Scheme 10 explains the enzymatic basis for the inhibition of catalase mediated by superoxide anions. On the one hand, superoxide anions are able to convert native catalase into the inactive Compound III ($CATFe^{III}O_2$) ①, on the other hand, to convert Compound I ($CATFeIV=O.^+$) by an one-electron transition into the inactive Compound II ($CATFe^{IV}=O$) and in this way substantially inhibit the enzyme effect.

Figure 11:
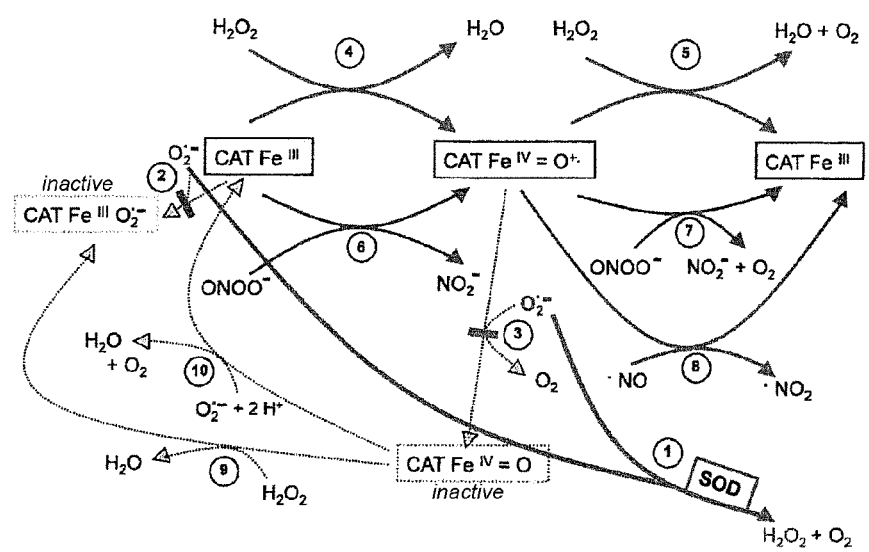

FIG. 11: Scheme 11 demonstrates that an SOD-mediated decrease in the concentration of superoxide anions below the concentration required for the inhibiting effect contributes to the establishment of the catalase activity.

Figure 12:
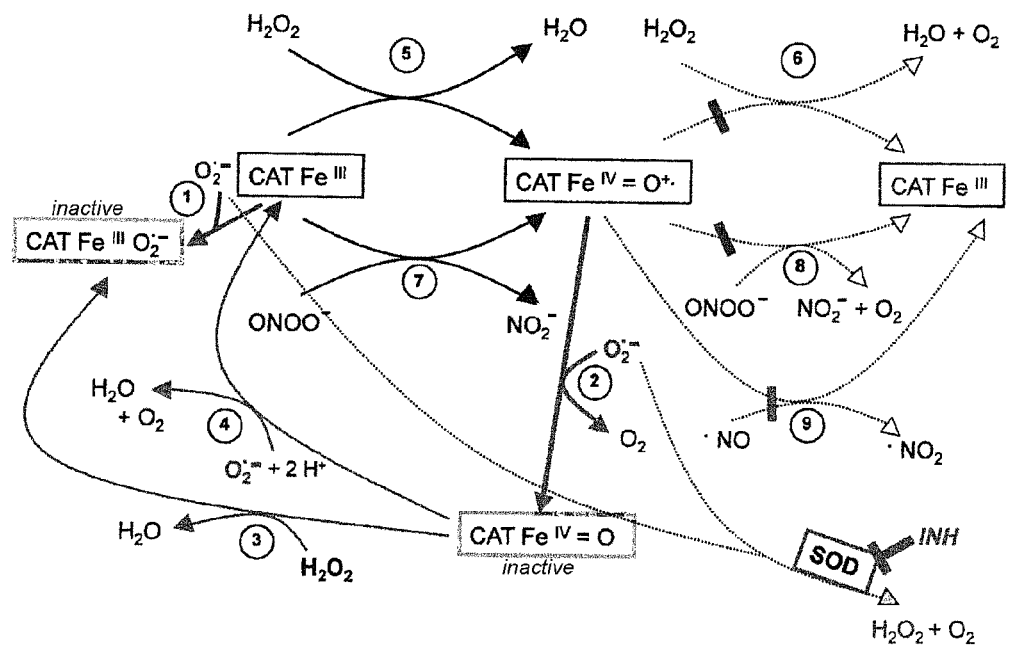

FIG. 12: Scheme 12 demonstrates that the direct inhibition of SOD necessarily involves an indirect inhibition of catalase.

Figure 13:
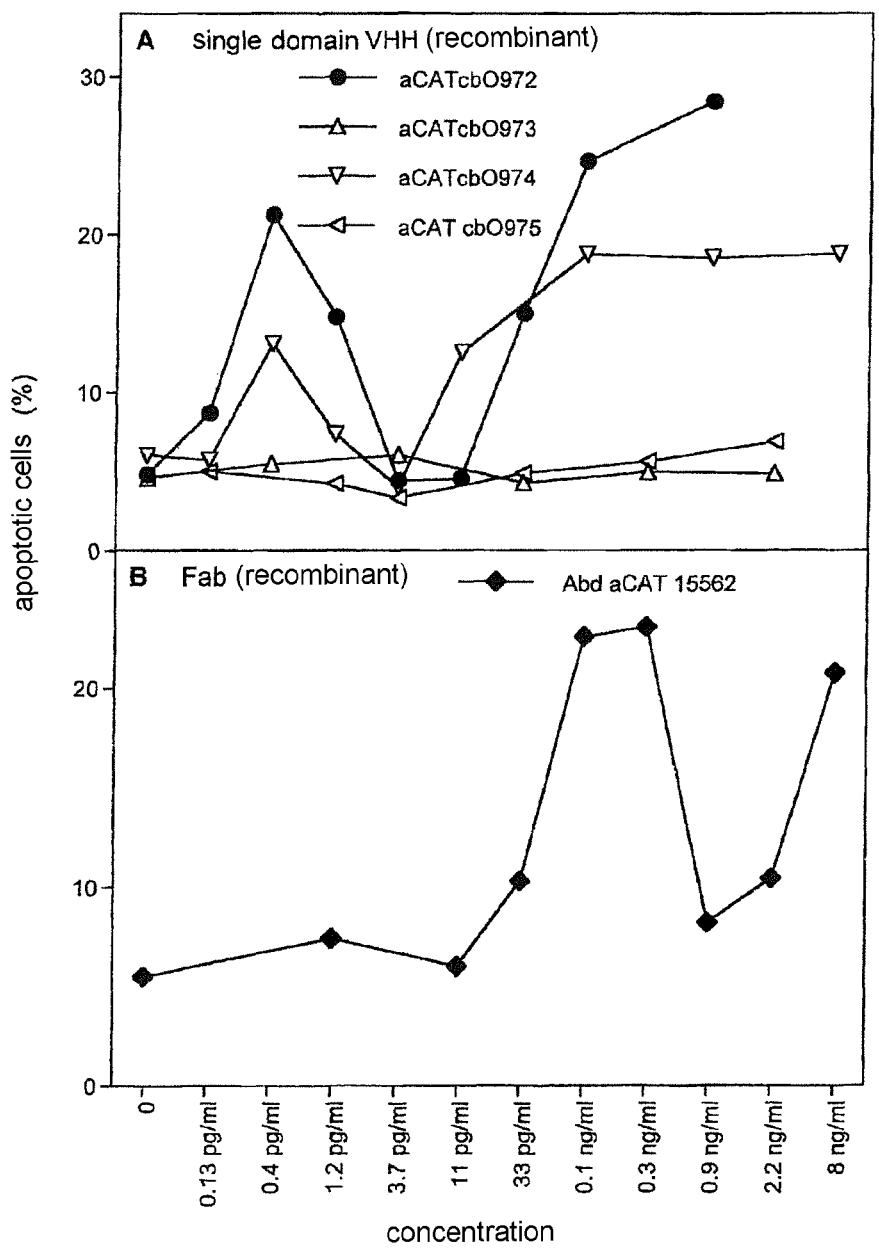

FIG. 13A shows the specific apoptosis induction in MKN-45 gastric carcinoma cells by single domain VHH fragments against catalase. FIG. 13B shows the induction of apoptosis that arises from the application under same conditions of recombinant Fab fragments (consisting of a light and a heavy chain) that are directed against and neutralize human catalase (Abd aCAT15562).

Figure 14:
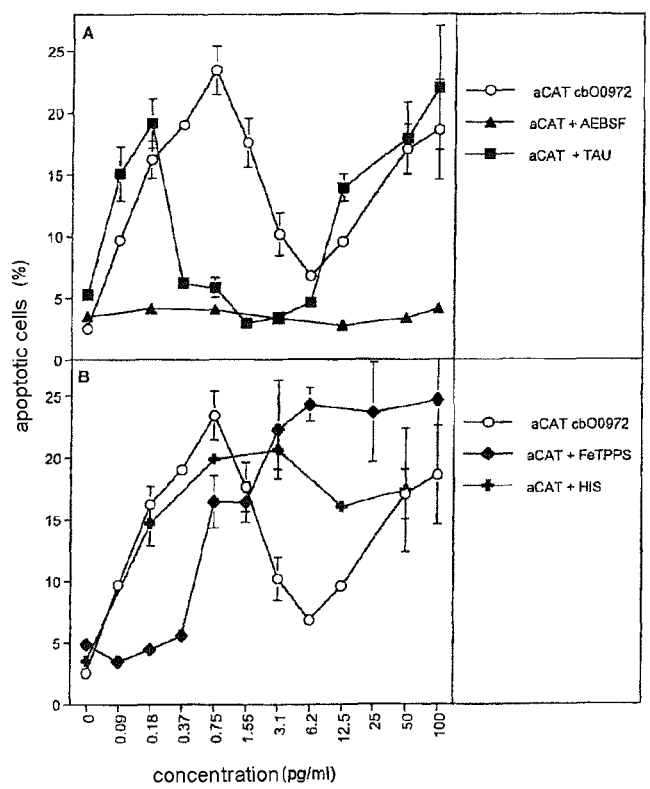

FIGS. 14A and 14B show that the catalase-neutralizing single domain VHH fragment aCATcb0972 in gastric carcinoma cells of the MKN-45 line induces specific ROS signaling via the NO/peroxynitrite and HOCl path.

Figure 15:
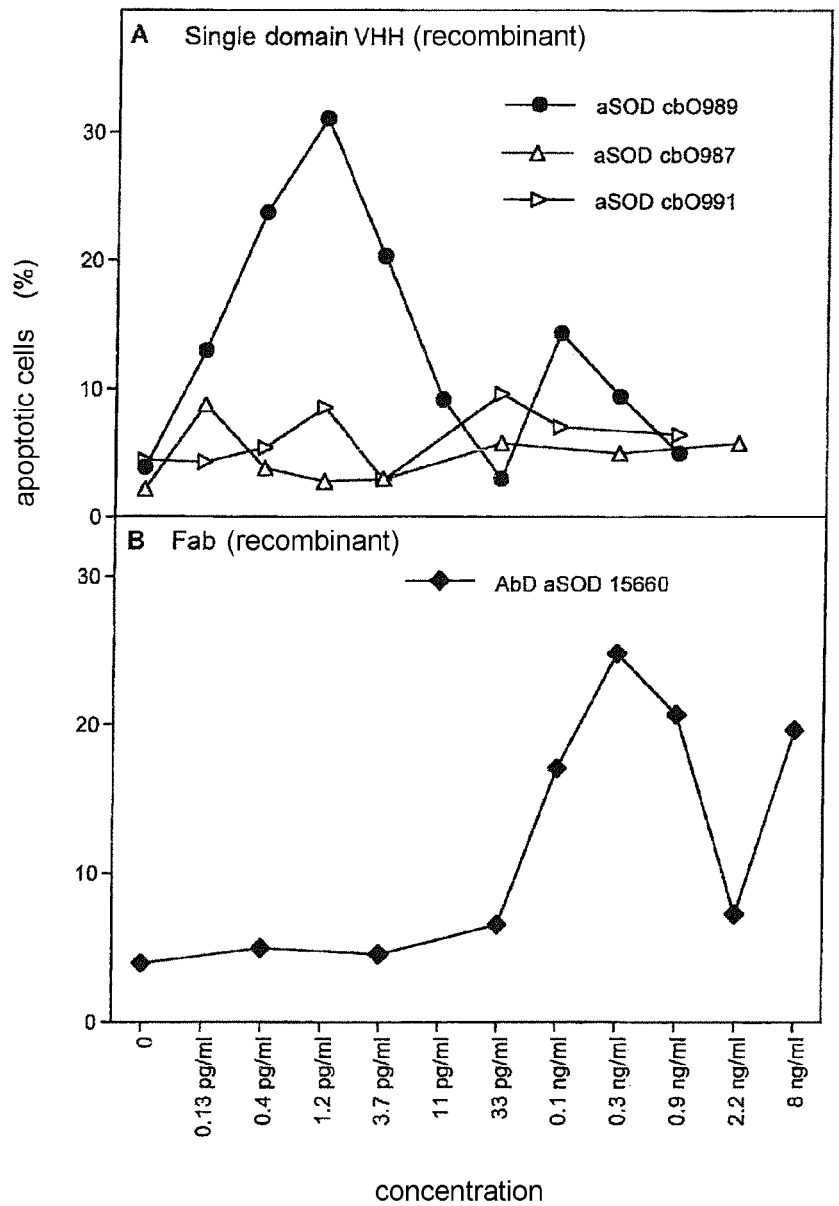

FIG. 15A shows the specific apoptosis induction in MKN-45 gastric carcinoma cells by single domain VHH fragments against SOD. FIG. 15B shows the induction of apoptosis that arises from the application under same conditions of recombinant Fab fragments (consisting of a light and a heavy chain) that are directed against and neutralize human catalase (Abd aSOD15660).

Figure 16:
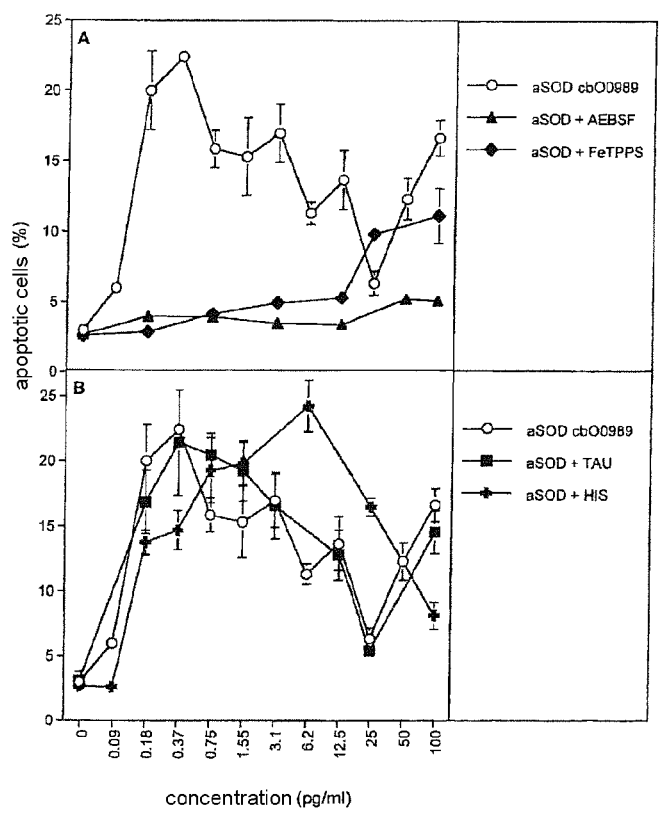

FIGS. 16A and 16B shows that the SOD-neutralizing single domain VHH fragment aSODcb0989 in gastric carcinoma cells of the MKN-45 line induces specific ROS signaling exclusively via the NO/peroxynitrite path. FIG. 16A depicts the induction of apoptosis arising from single domain VHH fragment aSODcb0989 alone or in the presence of 100 µM of the NOX1 inhibitor AEBSF or 25 µM of the peroxynitrite scavenger FeTPPS. FIG. 16B depicts the induction of apoptosis arising from single domain VHH fragment aSODcb0989 alone or in the presence of 50 mM of the HOCl scavenger taurine (TAU) or 2 mM of the singlet oxygen scavenger histidine (HIS).

Figure 17:
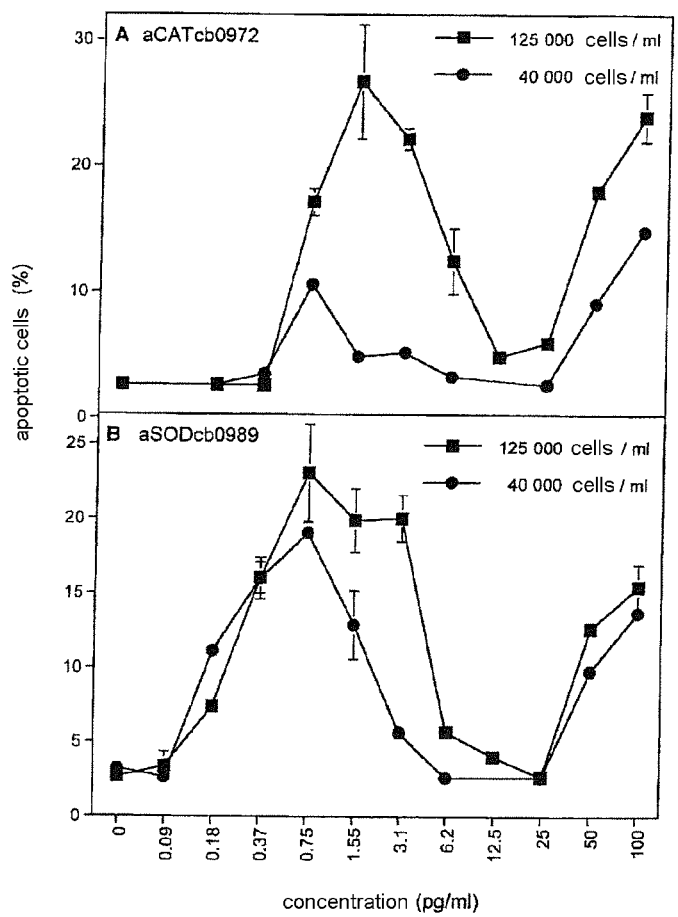

FIG. 17A shows that apoptosis induction by the single domain VHH fragments directed against catalase only with higher density runs in an optimum manner. FIG. 17B shows that when the application of the single domain VHH fragments is directed against SOD, there is much lesser attenuation of the effect when the target cells are present with a lower density.

FIGS. 18A and 18B show that the concentration-dependent apoptosis-inducing effects already measured in the preliminary experiments can be confirmed both by aCATcb0972 (FIG. 18A) and aSODcb0989 (FIG. 18B).

Figure 19:
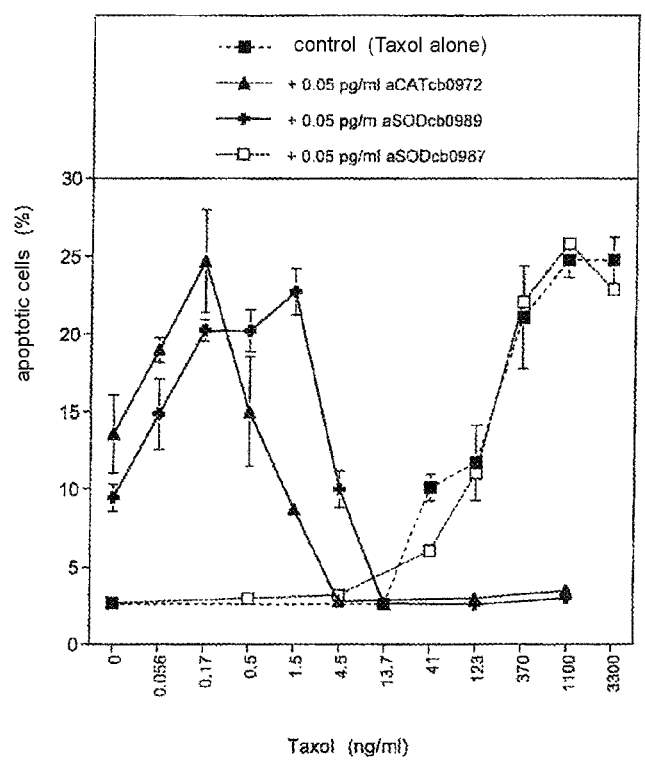

FIG. 19 shows that single domain VHH fragments neutralizing catalase or SOD, respectively, cause a strong synergistic effect with the established chemotherapeutic agent taxol.

Figure 20:
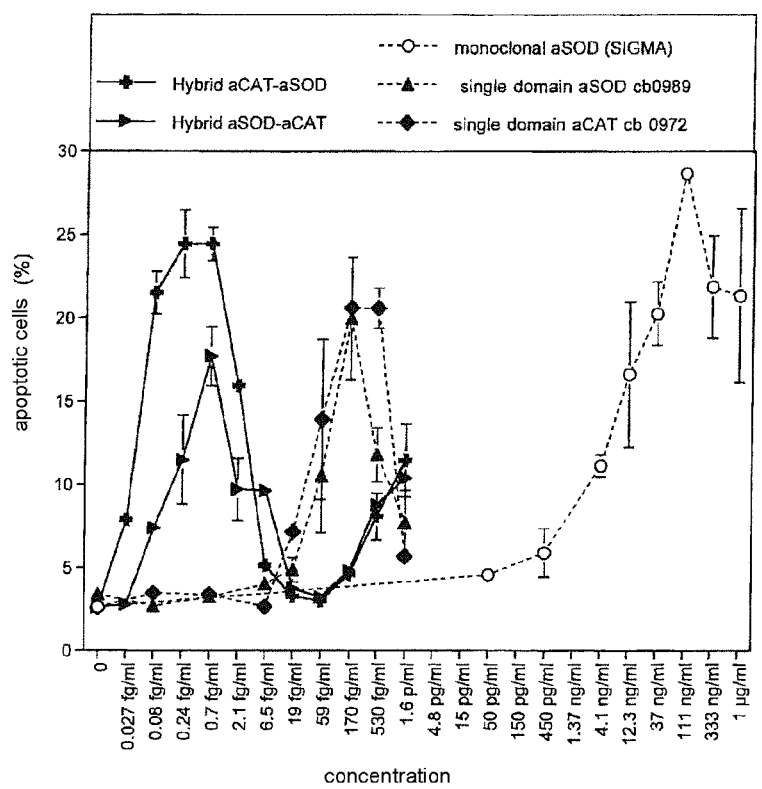

FIG. 20 shows that the synergistic effect between single domain VHH fragments aCAT and aSOD can be concentrated in one hybrid molecule.

Figure 21:
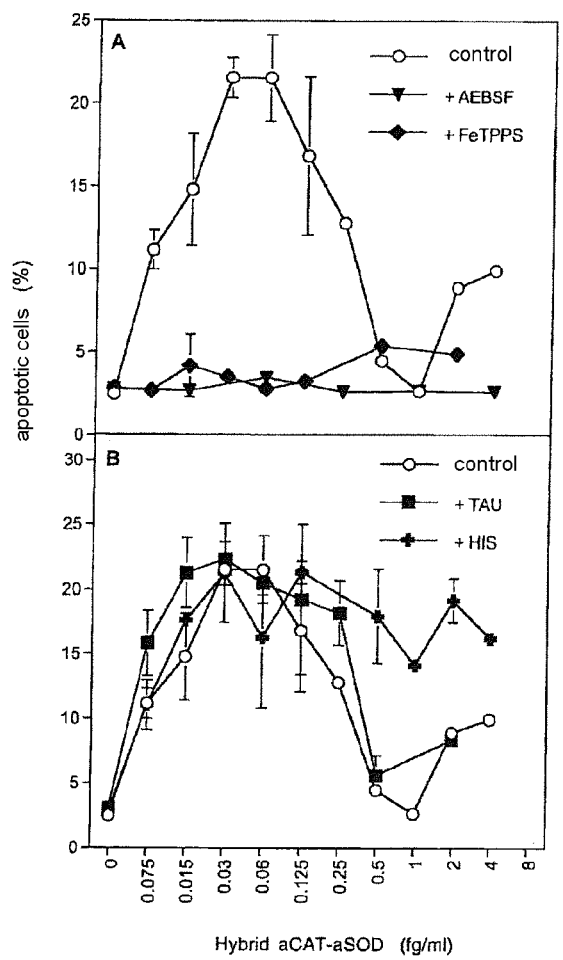

FIGS. 21A and 21B show that the hybrid molecule from the single domain VHH fragments aCATcb0972 and aSODcb0989 in gastric carcinoma cells of the MKN-45 line induces specific ROS signaling exclusively via the NO/peroxynitrite path. FIG. 21A depicts the induction of apoptosis arising the hybrid molecule in the presence of 100 µM of the NOX1 inhibitor AEBSF or 25 µM of the peroxynitrite scavenger FeTPPS. FIG. 21B depicts the induction of apoptosis arising from the hybrid molecule in the presence of 50 mM of the HOCl scavenger taurine (TAU) or 2 mM of the singlet oxygen scavenger histidine (HIS).

Figure 22:
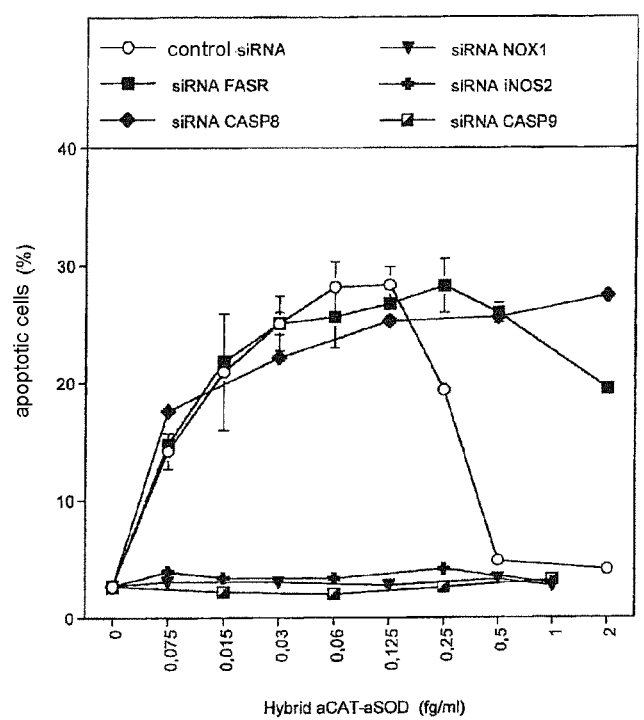

FIG. 22 presents the results of siRNA-based analysis confirming the specificity of the ROS signaling that is induced by the hybrid molecule and results in apoptosis.

FIGS. 23A and 23B shows that catalase- and SOD-neutralizing single domain VHH fragments (FIG. 23A) as well as the hybrid molecule aCATaSOD (FIG. 23B) can induce concentration-dependent apoptosis in the neuroblastoma line SHEP.

Figure 24:
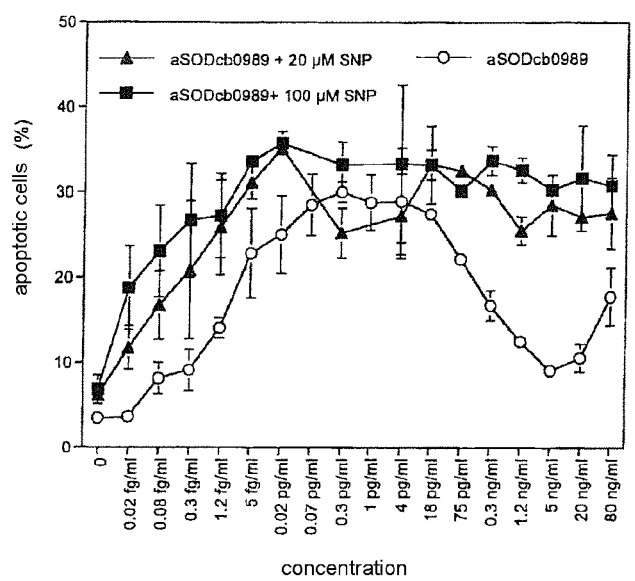

FIG. 24 shows that the additional administration of the NO donor (that alone is not able to induce apoptosis) both results in a sensitization concerning the reactivation of the apoptosis induction and effectively counteracts the supra-optimum right-side drop of the optimum curve.

Figure 25:
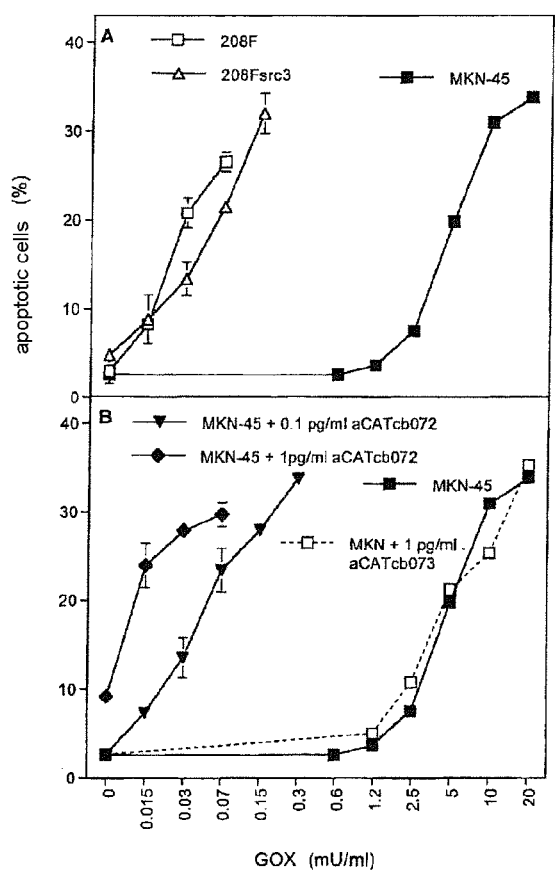

FIG. 25A shows that the tumor cell line MKN-45 is much better protected from $H_2O_2$ than the normal cells and the transformed cell line. FIG. 25B shows that, in the presence of catalase-neutralizing single domain VHH fragments, the tumor cells are very clearly sensitized for the effect of $H_2O_2$, whereas single domain VHH fragments that only bind to catalase do not result in a sensitization.

Figure 26:
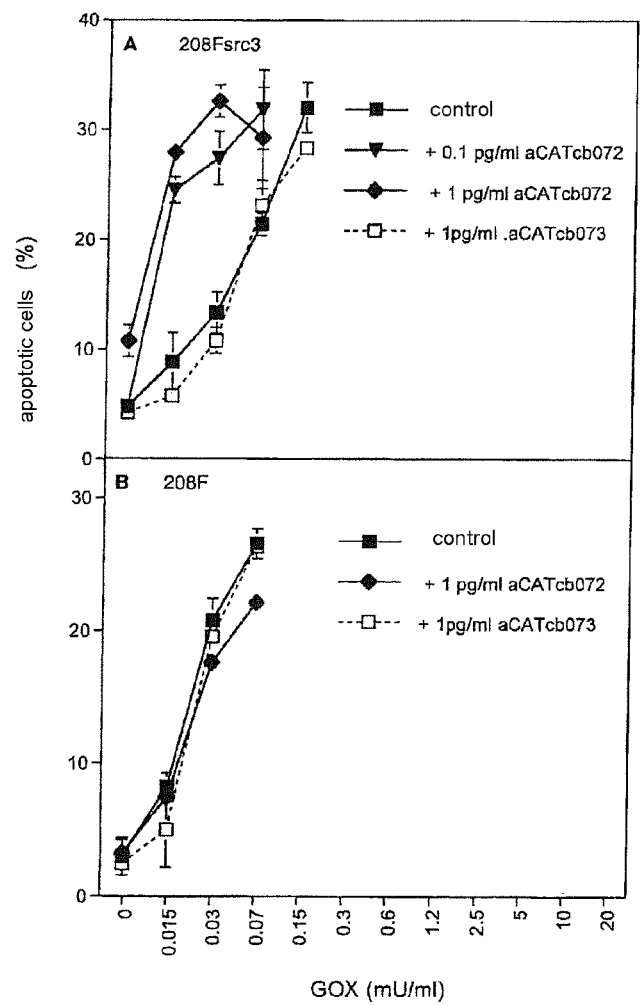

FIGS. 26A and 26B show that the neutralizing single domain VHH fragments caused a sensitizing effect on the transformed line that however could not influence normal cells.

FIG. 27A-27F shows that the siRNA-mediated knock-down of the intracellular catalase of normal cells (208F) (as compared to transformed cells (208Fsrc3) and tumor cells (MKN45)) increases their sensitivity against $H_2O_2$.

Figure 28:
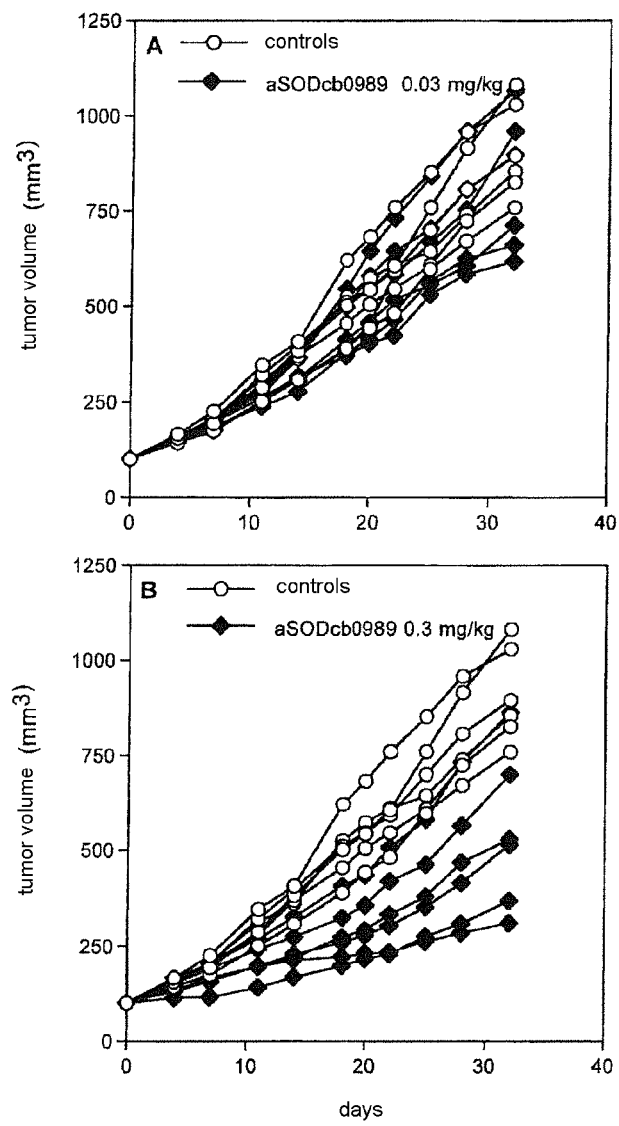

FIGS. 28A and 28B show that the growth of a human colon carcinoma xenotransplant on immunocompromised mice is inhibited by the repeated administration of the single domain VHH fragment aSODcb0989. FIG. 28A shows that, when applying 0.03 mg/kg of aSODcb0989, a recognizable difference to the controls does not result. FIG. 28B, however, shows that, when administering 0.3 mg/kg of aSODcb0989, the group treated with the single domain VHH fragment very clearly differs from the control group, even though both groups underlie a very strong spread (FIG. 28B).

Figure 29:
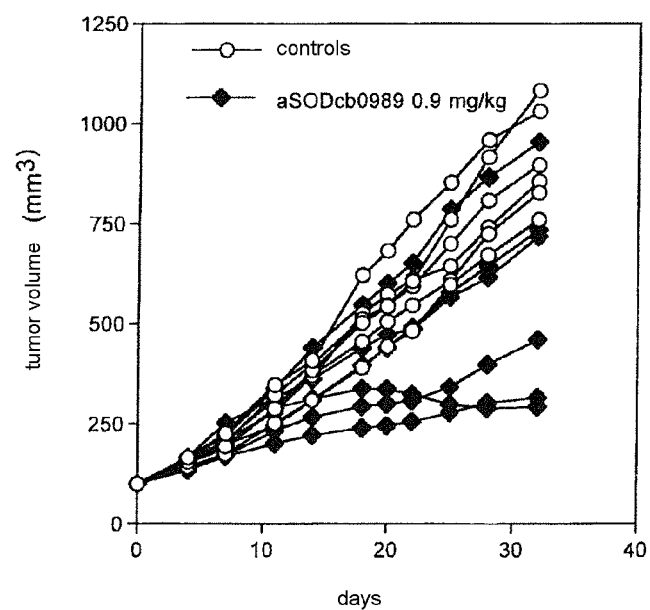

FIG. 29 shows that the growth of a human colon carcinoma xenotransplant on immunocompromised mice is inhibited by the repeated administration of the single domain VHH fragment aSODcb0989.

DETAILED DESCRIPTION OF THE PREFERRED EMBODIMENTS

Within the scope of the present invention there were prepared and sequenced various preferred antigen-binding fragments by genetic engineering. The sequences are disclosed in the present application. Particularly important for the antigen-binding sequences are the CDR regions of the constructs. The so-called "complementary determining regions" (in the following briefly CDR) are very specific parts of the variable chains of the immunoglobulins. Said CDR regions are embedded within the framework sequence of immunoglobulins, determine their specificity, and establish contact with the specific antigen to which the immunoglobulins bind. The CDR regions are the most variable parts of the immunoglobulins and substantially contribute to the variety of these molecules. In immunoglobulins having a heavy and a light chain there are six CDR regions. However, if the immunoglobulin only consists of one chain, such as in case of the single domain VHH fragments that are preferred according to the invention, there are three CDR regions.

Generally, it is important that the CDR regions are almost present unchanged if the bonding specificity is to be maintained. However, it is possible that minor mutations do not adversely affect the functionality of the antibody-binding constructs. This is especially true if the structure of the CDR is not adversely affected by the exchange of an amino acid. Such amino acid exchanges are possible if the newly inserted amino acid is very similar to the replaced amino acid. Thus, in a preferred embodiment the antigen-binding fragments have the CDR regions that were disclosed within the scope of the present application or they differ at most in a smaller number of amino acids from the respectively disclosed CDR sequences that do not substantially change or reduced the bondability and bonding specificity.

Within the scope of the present invention CDR regions of antigen-binding single domain VHH fragments are disclosed that descent from such constructs that either inhibit or not catalase and/or superoxide dismutase, but do bind thereto. In a preferred embodiment the single domain VHH fragments (nanobodies) according to the invention contain at least one, preferably at least two and most preferably at least three CDR regions, wherein those CDR regions descending from constructs that inhibit catalase and/or superoxide dismutase are especially preferred.

The constructs according to the invention can preferably be humanized when they are intended for therapeutic application. Here, the framework sequence is replaced by a human framework substance or the non-human sequence is changed into a human sequence by mutations, but the bonding properties are to be maintained.

For the development of therapeutically usable biological molecules (here nanobodies) often modifications of the amino acid sequence are unavoidable. Since the molecules do not descend from humans, but originally from camelidae it is possible or likely that antibodies against exogenous epitopes are generated. Such antibody reactions would neutralize the effect of the antibody fragment to be used in therapy. To avoid these difficulties the therapeutically used molecules are humanized. The humanization of antibodies or antibody fragments is a technology that is well known in this special field. Typically, it is looked for humane framework sequences (backbone) that have the highest possible similarity to the original molecule. Then, the CDR regions are excised from the original nanobody and transplanted into the human sequence. Here, it is not inevitable that certain adaptions of amino acid sequences have to be made.

A substantial aspect is that the site on the antigen to which the binding part of the antibody binds is defined by the CDR sequences. During the humanization it might be required to slightly modify one or two of the three CDR sequences in order that the advantageous properties of the antigen-binding part are maintained. Thus, the single domain VHH fragments according to the invention are characterized in that they contain at least one of the CDR sequences, preferably two and especially preferably three CDR sequences, as disclosed in the present application.

Thus, the object of the present invention are single domain VHH fragments that have at least one, preferably at least two and especially preferably at least three of the following CDR regions characterized by the SEQ ID numbers. These are the sequences with SEQ ID numbers 19, 20, 21, 22, 23, 24, 25, 26, 27, 28, 29, as well as 30. Further preferred CDR sequences derived from clones binding to SOD are CDRs with SEQ ID numbers 31, 32, 33, 34, 35, 36, 37, 38, and 39. Also preferred are CDR sequences with SEQ ID numbers 40, 41, 42, 43, 44, 45, 46, 47, 48, 49, 50, and 51.

In a further preferred embodiment the constructs according to the invention can further be provided with a marker. For this employment, it is not necessary that the constructs also inhibit the target enzyme in its function. Rather, a specific bond with sufficient affinity is sufficient. Such a bond can be measured in a classical ELISA system in which either human catalase or SOD is bound to a suitable carrier and the complex of enzyme and single domain VHH fragment is detected by a common detection method. On the one hand, a marker can be used to mark the desired tumor cells in order to arrive at diagnostic statements here. On the other hand, the marker may also serve to label the tumor cells for other effectors. For example, as markers such constructs can be employed that connect themselves to effectors that induce apoptosis of the tumor cells. One example of such a marker is an anti CD3 part reacting with the CD3 receptor of cytotoxic T cells. Such an anti CD3 part may be for example an antigen-binding part of an antibody directed against the CD3 receptor.

In further embodiments of the present invention an antigen-binding construct of the present invention may also be configured such that it can be connected to a cytotoxic agent. As the cytotoxic agent, there are known for example various toxins that descend from various sources, for example bacteria, fungi, or plants. Preferably, this may be the cholera toxin, the botulinus toxin, or streptolysin, to name just a few.

In a further embodiment, the antigen-binding constructs according to the invention can be connected to a cytotoxic agent via different types and possibilities of bonding. These could also be solid chemical bonds, such as covalent bonds as well as ionic interactions or van der Waals forces.

In a further embodiment, it is also possible that an antigen-binding construct according to the invention can be or is tightly connected to a radioactive isotope. The radioactive isotope either may serve for the diagnostic detection of the tumor cells or enhance the cytotoxic effect of the antigen-binding construct according to the invention by bringing a radioactive isotope into close proximity to a tumor cell. Preferably, in the therapeutic application such isotopes are employed that only radiate relatively short in order to keep the side effects as low as possible. Moreover, the half-life of the isotope should be relatively short in order to keep the burden of the body and the environment in an acceptable range. Preferably employed are yttrium-90, rhenium-186 or erbium-169.

In a further embodiment, the antigen-binding constructs according to the invention can be connected to a colorant via various types and possibilities of bonding. These can be solid chemical bonds such as covalent bonds as well as ionic interactions or van der Waals forces. The colorant can be detectable by different common methods. Such constructs should be usable for diagnostic purposes.

In a further embodiment, pharmaceutical compositions are disclosed that contain at least one antigen-binding construct according to the invention. These pharmaceutical preparations are preferably used to treat tumor diseases, in particular to treat gastric carcinoma.

The pharmaceutical compositions according to the invention contain at least one antigen-binding construct that specifically binds to and inhibits catalase. In another embodiment, the pharmaceutical compositions according to the invention contain at least one antigen-binding construct that specifically binds to and inhibits superoxide dismutase. In a further embodiment, the pharmaceutical composition contains a hybrid molecule that binds both to catalase and superoxide dismutase and inhibits both target enzymes.

It is surprising and was not predictable that the synergistic effect of the hybrid molecules exclusively reactivates the NO/peroxynitrite path, whereas anti-SOD alone also reactivates this path, but anti-catalase induces the HOCl path. The exclusive reactivation of the NO/peroxynitrite path by the hybrid molecules represents an advantage for the future applications, because the less complex NO/peroxynitrite path should be further optimized by an additional modulation of the NO metabolism, especially in view of a desired width of the plateau phase of the dose-effect relationship.

A further advantage of the exclusive reactivation of the NO/peroxynitrite path by anti-SOD or hybrid molecules from anti-SOD and anti-CAT is that due to the signal chemistry (ill. 1-4) in the course of the NO/peroxynitrite path no free $H_2O_2$ should be present. This is desired because $H_2O_2$ has a proliferation-stimulating effect on surviving tumor cells that is detrimental to the therapeutic effect. The principle of said advantage of the therapeutic use of anti-SOD or of the hybrid molecule from anti-catalase and anti-SOD disclosed here was not disclosed in EP 11170076.1 and has a surprising effect. This effect indicates the presence of an inventive step.

In a further preferred embodiment of the present invention there is used at least one antigen-binding construct of the present invention together with an active ingredient having antitumor activity. Various active ingredients having antitumor effects are known. Especially, as chemotherapeutics that can also be present in the present composition there can be mentioned substances such as taxol, cisplatin, endostatin, oxaliplatin, etopside, or colchicine, to name only a few active ingredients as examples. Preferably, taxol is employed.

The antigen-binding constructs according to the invention are single domain VHH fragments that can be prepared by genetic engineering.

A precise molecular arrangement of the individual fragments in the antigen-binding construct is of subordinate importance, as long as the desired function, namely binding to and inhibiting catalase and/or superoxide dismutase is preserved.

The antigen-binding constructs according to the invention are prepared with molecular-biological means. These are not naturally occurring antibodies or Fab fragments prepared therefrom by simple (enzymatic) cleavage. For better understanding, the structure of antibodies might be briefly recapitulated. Antibodies, for example of the IgG type, consist of two Fab fragments and one Fc fragment. Each Fab fragment consists of a light and a heavy chain, wherein the heavy chain can be divided into a variable part ($V_H$) and a constant part ($C_{H1}$) and the light chain can be divided into a variable part ($V_L$) and a constant part ($C_L$). Of particular interest are the variable parts $V_H$ and $V_L$ that in turn contain the CDRs (complementarity determining regions) 1-6 that are relevant for antigen-bonding. The bonding properties of the Fab fragments are determined by the CDR regions that are embedded in a framework structure that spatially arranges the individual CDR regions.

The antigen-binding constructs are single domain VHH fragments (nanobodies). Nanobodies contain only the parts of the heavy chain of the antibody relevant for binding and can be very good expressed in bacterial cells (Muyldermans S. Nanobodies: Natural single-domain antibodies. Ann. Rev. Biochem. 82: 775-797, 2013).

With the help of various methods of genetic engineering a number of antigen-binding constructs can be prepared. The methods used for that are quite diverse and well known to the person of average skill in the art. Typically, here it is proceeded such that laboratory animals (mice, rats, rabbits, chickens or camels, alpacas etc.) are immunized with the desired antigen. Since camels and alpacas in addition to the conventional antibodies naturally also possess IgG that is exclusively constructed of heavy chains the use of these animals in combination with established selective screening methods results in obtaining single domain antibody encoding nucleic acid sequences. Then, from suitable immunocytes (for example B cells) nucleic acid sequences can be isolated that are further optimized with suitable methods, for example with the so-called phage display. Then, with these methods antigen-binding construct molecules are obtained that specifically bind to the desired antigen. In this context, specifically means that the constructs preferably only bind to the molecule sought, more particularly only to an epitope of said molecule (SOD or catalase). Non-specific cross-reactions are generally undesired.

Another important property of said antigen-binding constructs is that they sensitively bind to the desired antigen. Sensitively means that already at a very low concentration of the antigen-binding construct a specific binding to the desired antigen or the desired epitope takes place. Expressed in simplified terms, the better an antigen-binding construct binds to the target antigen the more sensitive it is. Since the single domain VHH fragments do not enclose a certain epitope like classical Fab fragments do, but due to their molecular structure bind to spatial recesses of the antigen there result substantial differences with respect to the detectability of certain epitopes by these two types of single domain VHH fragments.

The antigen-binding constructs according to the invention specifically bind to the superoxide dismutase and inhibit this enzyme. The inhibition of the target molecule superoxide dismutase is effected by the fact that the antigen-binding construct either binds to the catalytically active center of the superoxide dismutase (SOD) or in the proximity of this catalytic center, whereby a steric inhibition of the enzyme is effected. Then, superoxide anions (the typical and specific substrate of SOD) can no longer bind to the enzyme and can not catalytically be converted to $H_2O_2$ by it.

The same applies to catalase. The antigen-binding constructs according to the invention specifically and sensitively bind to catalase and inhibit it so that the enzymatic conversion of $H_2O_2$ into $H_2O+\frac{1}{2} O_2$, or peroxynitrite into $NO_2^-$ and $\frac{1}{2} O_2$ is inhibited and the oxidation of NO by the active intermediate "Compound I" of the catalase is prevented.

In the present application the abbreviations given in the list below were used:
AEBSF 4-(2-aminoethyl)-benzenesulfonyl fluoride
 (inhibitor of the NADPH oxidase)
3-AT 3-aminotriazole
 (catalase inhibitor)
anti-CAT antibody against catalase
anti-SOD antibody against SOD
(For Reasons of Space in the Pictures the Designations Anti-CAT and Anti-SOD are Replaced by aCAT and aSOD)
CAT catalase
Compound I activated intermediate stage both of catalase of formula
 CAT $Fe^{IV}=O^+$. and peroxidase of formula POD $Fe^{IV}=O.^+$. Compound I is formed in the reaction of catalase or peroxidase with one molecule hydrogen peroxide. Catalase can also form Compound I with one molecule peroxynitrite.
Duox dual oxidase
 (membranous enzyme consisting of a NADPH oxidase and a peroxidase domain. The peroxidase domain is cleaved off with the help of proteases.)
FBS fetal bovine serum
FeTPPS 5-, 10-, 15-, 20-tetrakis(4-sulfonatophenyl)porphyrinato iron(III) chloride
 (peroxynitrite decomposition catalyst)
NO nitric oxide
NOD nitric oxide dioxygenase (oxidizes NO to nitrate)
NOS NO synthase
NOX NADPH oxidase (here, in particular the membranous NOX-1)
POD peroxidase
 (in this context in particular the ability of certain peroxidases takes effect that in the presence of hydrogen peroxide they are able to oxidize chloride to HOCl)
PON peroxynitrite
POR cytochrome P 450 oxidoreductase
RAS, RAC oncogenes
ROS reactive oxygen and nitrogen species
 (radical and non-radical species such as superoxide anions, hydroxyl radicals, nitric oxide, hydrogen peroxide, HOCl, peroxynitrite, etc.)
siRNA small interfering RNA
 (reagent to specifically down-regulate the synthesis of defined gene products)
SOD superoxide dismutase
 (here, in particular SOD-1 ($Cu^{++}$ in the active center of the tumor cells and MnSOD from bacteria for analytical purposes)
TGF-beta transforming growth factor type beta

EXAMPLES

The present invention is explained in detail by the following examples. The results of the experiments according to the invention are often illustrated in the figures. There are disclosed sequences of particularly preferred embodiments.

Example 1: Provision of Constructs and Materials

The following examples were carried out with the following antibodies, Fab fragments, or single domain VHH fragments:
1) Monoclonal antibody (mouse, IgG1) against human SOD-1 (clone SD-G6) (charge number 035K4823). Manufacturer Sigma Aldrich, Schnelldorf, Germany (as a control).
2) Recombinant human Fab fragment against human catalase, format Fab-V5Sx2, prepared by AbDSerotec from a Human Combinatorial Antibody Libraries or HUCAL® Library, i.e., a compilation of human antibody genes such as described in detail in EP 859 841 and U.S. Pat. No. 6,300,064 that have been made synthetically to cover more than 95% of the structural human immune repertoire, cloned in *E. coli* phagemid vectors. There was employed the construct # AbD15562 with catalase-inhibiting effect (comparison).
3) Recombinant human Fab fragment against human SOD, format Fab-V5Sx2, prepared by AbDSerotec from a HUCAL® Library as described above. There was employed construct # AbD15660 with SOD-inhibiting effect (comparison).
4) Recombinant single domain VHH fragments against human catalase (according to the invention), prepared in cooperation with a commercial supplier.

The preparation was by immunizing alpacas with human catalase (catalase [EC 1.11.16] purified from human erythrocytes, obtained from Sigma (Schnelldorf), catalogue number C 3556) under the supervision of a veterinary, obtaining RNA from the B cells of the animals, reverse transcription, cloning in E. coli and isolation via phage display technology. Clones encoding for single domain VHH fragments that bind to human catalase were selected by testing supernatants in a suitable ELISA. In a second run, by employing the cell culture system described by Heinzelmann and Bauer (Heinzelmann S. and Bauer G. Multiple protective functions of catalase against intercellular apoptosis-inducing ROS signaling of human tumor cells, Biol. Chem. 391, 675-693, 2010) it was checked which one of the single domain VHH fragments binding to catalase actually results in an inhibition of the catalase, what is expressed as ROS-dependent apoptosis induction in the cells. There were used the single domain VHH fragments aCATcb0972, aCATcb0974, that both bind to human catalase and neutralize it, and aCATcb0973 and aCATcb0975, that bind to human catalase, but do not neutralize it. The clones underlying the single domain VHH fragments were sequenced by standard methods and the amino acid sequence was determined therefrom.

Preferred embodiments of the invention have the following sequences.

The sequences of the antigen-binding fragments were analyzed both for DNA and protein level and the antigen-binding regions (CDR) were determined. In the following only the amino acid sequences are described. These antigen-binding regions are substantial for the specificity of the antigen-binding fragments.

In a preferred embodiment of the present invention the antigen-binding constructs, especially the single domain VHH fragments or nanobodies, contain at least one CDR sequence, preferably at least two and most preferably three CDR sequences.

In the following, there are described the CDR sequences at the protein level. In the complete sequence the respective positions are given by underlining.

```
cb 0972 (binding to and neutralizing catalase):
protein sequence (SEQ ID NO: 10):
MAQVQLVESGGGLVQAGGSLRLSCAASERTFNTYGMGWFRQAPGKEREFV

ATISWSGDSTYYADSVKGRFTISRDNAKNTMYLQMNSLKPEDTAVYYCNA

NSEYGDSYWGQGTQVTVSSKKKHHHHHH

CDR sequence at protein level:
CDR1: RTFNTYGMG (SEQ ID NO: 19)

CDR2: TISWSGDSTYYADSVKG (SEQ ID NO: 20)

CDR3: NSEYGDSY (SEQ ID NO: 21)

cb 0973 (binding to catalase, but not
neutralizing):
protein sequence (SEQ ID NO: 11):
MAEVQLVESGGGLVQPGGSLRLSCAVSGFIFNTYSMRWGRQAPGKGLEWV

SSISTGGYSTYADSVKGRFTISRDNAKNLVYLQMNSLKPEDTAVYYCGWG

AFVRGERPQGQGTQVTVSSKKKHHHHHH

CDR sequence at protein level:
CDR1: FIFNTYSMR (SEQ ID NO: 22)

CDR2: SISTGGYSTYADSVKG (SEQ ID NO: 23)

CDR3: GAFVRGERP (SEQ ID NO: 24)

cb 0974 (binding to and neutralizing catalase):
protein sequence (SEQ ID NO: 12):
MAQVQLVESGGGLVQPGGSLRLSCAASGSIFSIASMGWYRQAPGKQRDLV

ATITSDGSTKYADSVKGRFTISRDNAKNTMYLQMNSVKPEDAAVYYCNAD

ADDLEPGSYDYDYWGQGTQVTVSSKKKHHHHHH

CDR sequence at protein level:
CDR1: SIFSIASMG (SEQ ID NO: 25)

CDR2: TITSDGSTKYADSVKG (SEQ ID NO: 26)

CDR3: DADDLEPGSYDYDY (SEQ ID NO: 27)

cb 0975 (binding to catalase, but not
neutralizing):
protein sequence (SEQ ID NO: 13):
MAQVQLVESGGGLVQPGGSLRLSCAASASIFSIYVMAWYRQAPGKQRELV

ATVTSGGATNYANSVKGRFTISRDNAKNTMDLQMNSLKPEDTAVYYCNAE

DYYDYGLSRSKIYWGQGTQVTVSSKKKHHHHHH

CDR sequence at protein level:
CDR1: SIFSIYVMA (SEQ ID NO: 28)

CDR2: TVTSGGATNYANSVKG (SEQ ID NO: 29)

CDR3: EDYYDYGLSRSKIY (SEQ ID NO: 30)
```

5) Recombinant single domain VHH fragments against human SOD1, prepared in cooperation with a commercial supplier.

The preparation was by immunizing alpacas with human SOD1 (SOD1=Cu/ZnSOD [EC 1.15.1.1] purified from human erythrocytes, obtained from Sigma (Schnelldorf), catalogue number S 9636) under supervision of a veterinary, obtaining RNA from the B cells of the animals, reverse transcription, cloning in E. coli and isolation via the phage display technology. Clones encoding for single domain VHH fragments that bind to human SOD1 were selected by testing supernatants in a suitable ELISA. In a second run, by employing the cell culture system described by Heinzelmann and Bauer (Multiple protective functions of catalase against intercellular apoptosis-inducing ROS signaling of human tumor cells, Biol. Chem. 391, 675-693, 2010) it was checked which of the single domain VHH fragments binding to SOD actually results in an inhibition of SOD, what is expressed in the tumor system used as ROS-dependent apoptosis induction in the cells, since by the inhibition of SOD the concentration of free superoxide anions dramatically increases due to the absence of the enzymatic dismutation and results in a parallel indirect inhibition of catalase. In the following, this is expressed as ROS-dependent apoptosis induction. In a further control trial the specific inhibition of SOD by recombinant single domain VHH fragments was verified by the fact that the increasing effect of these fragments on apoptosis induction by exogenously added HOCl was examined, as described in Bauer 2013 (HOCl-dependent singlet oxygen and hydroxyl radical generation modulate and induce apoptosis of malignant cells. Anticancer Res 33: 3589-3602, 2013). There was used the single domain VHH fragment aSODcb0989 that binds to and neutralizes human SOD1, and the fragments aSODcb0987 and aSODcb0991 that bind to human SOD1, but do not neutralize it.

The clones underlying the single domain VHH fragments were sequenced by standard methods and the amino acid sequence was determined therefrom. Preferred embodiments of the invention have the following sequences:

```
anti-SOD VHHs:
cb 0987 (binding to SOD, but not neutralizing):
protein sequence (SEQ ID NO: 14):
MAQVQLVESGGGIVQPGGSLRLSCVASESISEIDAMYWHRQAPGKERELV

AGITNDGTRYYADSVKGRFTISRDNAKSTLYLQMNSLKFEDTAMYYCAAL

PNPPPGYWGQGTQVTVSSKKKHHHHHH

CDR sequence at protein level:
CDR1: SISEIDAMY (SEQ ID NO: 31)

CDR2: GITNDGTRYYADSVKG (SEQ ID NO: 32)

CDR3: LPNPPPGY (SEQ ID NO: 33)

cb 0989 (binding to and neutralizing SOD):
protein sequence (SEQ ID NO: 15):
MAQVQLVESGGGLVQSGGSLTLSCTASGFTISNYPMTWVRQAPGKGLEWV

SRINSGGDRTLYADSVKGRFTVSRDNARNTMYLQMNNLKPEDTGLYFCAD

SGAGWRYWGQGTQVTVSSKKKHHHHHH

CDR sequence at protein level:
CDR1: FTISNYPMT (SEQ ID NO: 34)

CDR2: RINSGGDRTLYADSVKG (SEQ ID NO: 35)

CDR3: SGAGWRY (SEQ ID NO: 36)

cb 0991 (binding to SOD, but not neutralizing):
protein sequence (SEQ ID NO: 16):
MAQVQLVESGGGIVQPGGSLRLSCVASESISDIDAMYWHRQAPGKRRELV

AGITNDGTEYFADSVKGRFAISRDNTKSSLYLQMNSLKLEDTAMYYCATL

PNPPPGYWGQGTQVTVSSKKKHHHHHH

CDR sequence at protein level:
CDR1: SISDIDAMY (SEQ ID NO: 37)

CDR2: GITNDGTEYFADSVKG (SEQ ID NO: 38)

CDR3: LPNPPPGY (SEQ ID NO: 39)
```

By connecting clones cb 0972 (neutralizing catalase) and cb 0989 (neutralizing SOD) via a linker the bispecific hybrid single domain VHH fragments cb 1081 (anti-CATanti-SOD) and cb 1082 (anti-SODanti-CAT) were prepared by genetic engineering.

```
Bispecific anti-Catalase-SOD VHH
cb 1081:
protein sequence (SEQ ID NO: 17):
MAQVQLVESGGGLVQAGGSLRLSCAASERTFNTYGMGWFRQAPGKEREFV

ATISWSGDSTYYADSVKGRFTISRDNAKNTMYLQMNSLKPEDTAVYYCNA

NSEYGDSYWGQGTQVTVSSGGGGSGGGGSGGGGSAQVQLVESGGGLVQSG

GSLTLSCTASGFTISNYPMTWVRQAPGKGLEWVSRINSGGDRTLYADSVK

GRFTVSRDNARNTMYLQMNNLKPEDTGLYFCADSGAGWRYWGQGTQVTVS

SKKKHHHHHH

CDR sequence at protein level:
CAT CDR1: RTFNTYGMG (SEQ ID NO: 40)

CAT CDR2: TISWSGDSTYYADSVKG (SEQ ID NO: 41)

CAT CDR3: NSEYGDSY (SEQ ID NO: 42)

SOD CDR1: FTISNYPMT (SEQ ID NO: 43)

SOD CDR2: RINSGGDRTLYADSVKG (SEQ ID NO: 44)

SOD CDR3: SGAGWRY (SEQ ID NO: 45)

Bispecific anti-SOD-Catalase VHH
cb 1082
protein sequence (SEQ ID NO: 18):
MAQVQLVESGGGLVQSGGSLTLSCTASGFTISNYPMTWVRQAPGKGLEWV

SRINSGGDRTLYADSVKGRFTVSRDNARNTMYLQMNNLKPEDTGLYFCAD

SGAGWRYWGQGTQVTVSSGGGGSGGGGSGGGGSAQVQLVESGGGLVQAGG

SLRLSCAASERTFNTYGMGWFRQAPGKEREFVATISWSGDSTYYADSVKG

RFTISRDNAKNTMYLQMNSLKPEDTAVYYCNANSEYGDSYWGQGTQVTVS

SKKKHHHHHH

CDR sequence at protein level:
SOD CDR1: FTISNYPMT (SEQ ID NO: 46)

SOD CDR2: RINSGGDRTLYADSVKG (SEQ ID NO: 47)

SOD CDR3: SGAGWRY (SEQ ID NO: 48)

CAT CDR1: RTFNTYGMG (SEQ ID NO: 49)

CAT CDR2: TISWSGDSTYYADSVKG (SEQ ID NO: 50)

CAT CDR3: NSEYGDSY (SEQ ID NO: 51)
```

The NADPH oxidase inhibitor 4-(2-aminoethyl-benzene-sulfonyl fluoride (AEBSF), the catalase inhibitor 3-amino-triazole (3-AT), the HOCl scavenger taurine, the singlet oxygen scavenger histidine, glucose oxidase (GOX) were obtained from Sigma (Schnelldorf, Germany). Peroxynitrite and the "peroxynitrite decomposition catalyst" (functional peroxynitrite scavenger) 5-, 10-, 15-, 20-tetrakis(4-sulfonatophenyl)porphyrinato iron(III) chloride (FeTPPS) were obtained from Calbiochem (Merck Biosciences GmbH, Schwalbach/Ts, Germany).

A precise description of these active ingredients is found in the publications Heinzelmann and Bauer (2010, Multiple protective functions of catalase against intercellular apoptosis-inducing ROS signaling of human tumor cells, Biol. Chem. 391, 675-693), and Bechtel and Bauer (2009, Catalase protects tumor cells against apoptosis induction by intercellular ROS signaling, Anticancer Res 29: 4541-4557).

Example 2: Gene Knockout with siRNAs

For the analysis described in FIG. 22 by employing the specific knockout of genes by means of the siRNA technique the following siRNAs (obtained from Qiagen, Hilden, Germany) were applied:
A. control siRNA ("siCo"), (catalogue no. 1022076; sequence:

```
                              (SEQ ID NO: 1)
   r(UUCUCCGAACGUGUCACGU)dTdT (sense)

(SEQ ID NO: 2)
   ACGUGACACGUUCGGAGAA)dTdT (antisense).
```

The manufacturer has found that siCo does not influence the expression of any known gene.
B. "High-performance validated siRNAs" for the knockdown of: FAS receptor ("siRNA FAS R.")

(Hs_FAS_7_HP validated siRNA, catalogue No. (SEQ ID NO: 3)
SI02654463; target sequence: AAG GAG TAC ACA GAC AAA GCC);

caspase-8 ("siRNA CASP8")

(Hs_CASP8_11_HP validated siRNA; catalogue No. (SEQ ID NO: 4)
SI02661946, target sequence: AAG AGT CTG TGC CCA AAT CAA);

caspase-9 ("siRNA CASP-9")

(Hs_CASP9_7_HP validated siRNA, catalogue No. (SEQ ID NO: 5)
SI02654610, target sequence: CAG TGA CAT CTT TGT GTC CTA);

C: HP siRNA against human NOX1 ("siRNA NOX1"); target sequence:

(SEQ ID NO: 6)
CCG ACA AAT ACT ACT ACA CAA

D: siRNA against human iNOS2 (siiNOS) target sequence:

(SEQ ID NO: 7)
CTG GGC CGT GCA AAC CTT CAA

Figure 27:
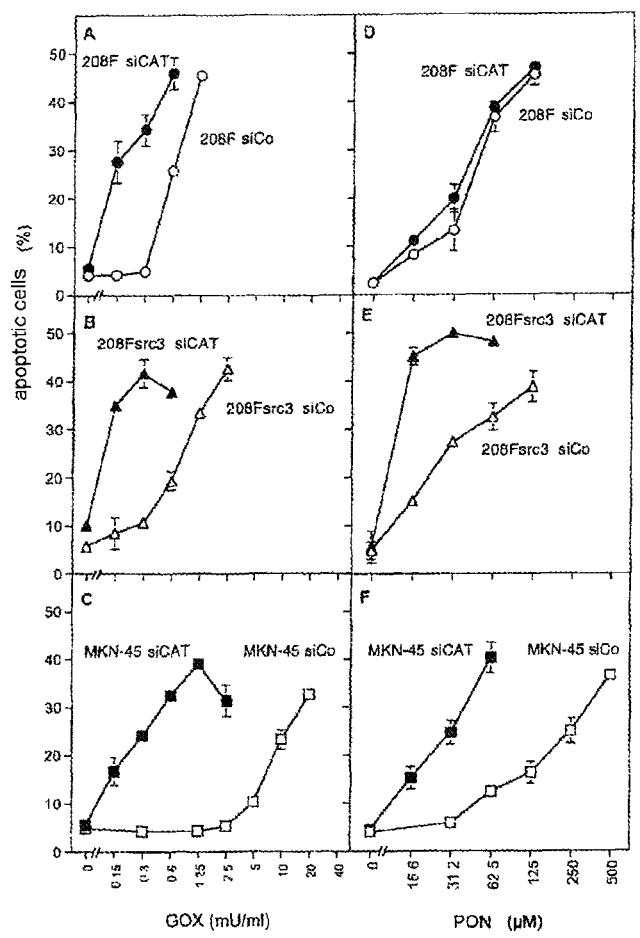

For the control examinations represented in FIG. 27 in addition to control siRNA there were also used siRNA against human catalase (for MKN-45 cells)
Hs_CAT_4_HP siRNA, catalogue No. SI00027713
target sequence:

(SEQ ID NO: 8)
CCG GAT CTC ACT TGG CGG CAA and siRNA against murine catalase (for 208F and 208Fsrc3 cells)
HP Mm_Cat_4_HP siRNA, catalogue No. SI00941976
target sequence:

(SEQ ID NO: 9)
CCC AAT AGG AGA TAA ACT TAA.

The transfection technique by means of the siRNAs is described in detail in Heinzelmann and Bauer, 2010 (loc.cit.). The transfection efficiency was more than 95%. 24 hours after the transfection control examinations for the respective gene functions were carried out that made sure that the "functional knockdown" was complete. This means that the specific siRNAs had effectively suppressed the De-Novo synthesis of the analyzed gene products and that the natural degradation of the concentration of the gene products before the administration of siRNA took place up to below the detection limit.

The human gastric carcinoma line MKN-45 was kept in RPMI 1640 medium, supplemented with 10% inactivated fetal bovine serum and 40 U/ml penicillin, 50 µg/ml streptomycin, g/ml neomycin, 10 U/ml Moronal (antimycotic antibiotic agent) and 280 µg/ml glutamine. The human neuroblastoma line SHEP as well as normal rat fibroblasts (208F) and their offspring transformed by the src oncogene (208Fsrc3) were kept in eagle's minimum essential medium (EMEM) supplemented with 5% inactivated fetal bovine serum and 40 U/ml penicillin, 50 µg/ml streptomycin, 10 µg/ml neomycin, 10 U/ml Moronal and 280 µg/ml glutamine. Details on the cell lines and their culture are found in the works of Heinzelmann and Bauer, 2010 and Bechtel and Bauer, 2009.

Example 3: Standard Preparation for the Analysis of the Autocrine ROS-Controlled Apoptosis Induction in Tumor Cells The experiments shown in FIG. 13-24 were carried out with a standard preparation for the apoptosis induction that is based on the method performed in Heinzelmann and Bauer 2010. The tumor cells used were taken from an optimally growing semi-sealed culture, centrifuged and placed in fresh medium. The test was performed in 96-well cell culture plates with 12 500 MKN-45 cells/100 µl medium or 10 000 SHEP cells/100 µl medium. MKN-45 cells grow in suspension, SHEP cells are adherent. The tests with SHEP cells were started as soon as the cells had grown on. By adding increasing concentrations of single domain VHH fragments that either inhibit catalase or SOD the protection of the tumor cells from their own ROS signaling was annulled so that based on the cell-owned extracellular superoxide anion production the NO/peroxynitrite signal path and the HOCl path (with MKN-45 cells) or in case of the SHEP cells only the NO/peroxynitrite path could start when the cells were incubated at 37° C. The analysis of the signal paths was carried out by the application of inhibitors of the NADPH oxidase (AEBSF), the HOCl scavenger taurine, the peroxynitrite scavenger FeTPPS and the singlet oxygen scavenger histidine. In some experiments for comparison instead of the single domain VHH fragments either recombinant Fab fragments or monoclonal antibodies were applied. This is indicated in the respective illustrations.

Double preparations were examined at the times shown in the text by means of phase contrast reverse microscopy for the percentage of apoptotic cells. Here, the classical apoptosis criteria described and documented in Heinzelmann and Bauer 2010 such as condensation of the nucleus, fragmentation of the nucleus, and membrane blebbing were used. Per single preparation at least 250 randomly selected cells were examined for the presence of apoptosis features.

Parallel control examinations, as e.g. documented in the work of Bauer et al. (Bauer G, Bereswill S, Aichele P and Glocker E. *Helicobacter pylori* protects oncogenically transformed cells from reactive oxygen species-mediated intercellular induction of apoptosis, Carcinogenesis 35: 1582-1591, 2014, Supplement) made sure that the applied morphological criteria correlated with apoptosis criteria such as DNA fragmentation (measured by the TUNEL reaction) or positivity for annexin V binding.

Example 4: Specific Sensitization of Tumor Cells for Apoptosis-Inducing ROS Signaling by Single Domain VHH Fragments Against Catalase In the scope of the present invention many trials have been carried out with the results of the trials having been summarized in FIGS. 13 to 29, summarized above.

FIG. 13A shows the specific apoptosis induction in MKN-45 gastric carcinoma cells by single domain VHH fragments against catalase.

MKN-45 cells under standard conditions for autocrine apoptosis induction were mixed with the given concentrations of single domain VHH fragments that bind to but do not inhibit human catalase (aCATcb0973, aCATcb0975) and single domain VHH fragments that bind to and inhibit human catalase (aCATcb0972; aCATcb9074) and were further incubated for 3.5 hours at 37° C., 5% $CO_2$. In parallel under same conditions recombinant Fab fragments (consisting of a light and a heavy chain) were applied that are directed against and neutralize human catalase (Abd aCAT15562; FIG. 13B). Thereafter, the percentage of apoptotic cells (double preparations) was determined in accordance with the above-mentioned classical apoptosis criteria.

FIGS. 13A and 13B show that only single domain VHH fragments inhibiting catalase, but not such that bind to the enzyme without inhibiting it induce apoptosis in the tumor cells. Here, the effect is represented in the form of an optimum curve, as has also been described in the work of Heinzelmann and Bauer, 2010 for the catalase inhibitor 3-aminotriazole. After the optimum curve has dropped there is a second increase in apoptosis induction. The addition of the recombinant Fab fragment Abd aCAT 15562 consisting of light and heavy chains also results in the apoptosis induction in the form of an optimum curve with a subsequent second increase, but to achieve the action optimum there is required a molar concentration of Abd aCAT 15562 that is about 250-fold higher in comparison to the catalase-inhibiting single domain VHH fragments. This is made evident by the superior efficacy of the constructs according to the invention.

The addition of single domain VHH fragments and classical Fab fragments inhibiting human catalase in the gastric carcinoma cell line MKN-45 results in the induction of apoptosis in the form of an optimum curve with respect to the concentration of the antibodies. The specificity of the induced process is made evident by the fact that single domain VHH fragments that bind to catalase but do not neutralize it do not result in an apoptosis induction (FIG. 13A, 13B). That is, for the sensitization it is not sufficient that antibodies only bind to the catalase. The specific inhibition of the function of catalase seems to be essential for the sensitization. Noteworthy and unexpected is the finding that the single domain VHH fragments have a much stronger apoptosis-inducing effect than classical Fab fragments. Due to the different structure of these two groups of fragments it would have been to be expected that the classical Fab fragments would have been to be applied with twice the concentration in comparison with single domain VHH fragments in order to achieve a similar effect. However, the difference makes up a factor of about 500 (on a molar basis of 250).

Example 5: Effect of a Single Domain VHH Fragment Binding Catalase and Inhibition in Gastric Carcinoma Cells FIG. 14A shows that the catalase-neutralizing single domain VHH fragment aCATcb0972 in gastric carcinoma cells of the MKN-45 line induces specific ROS signaling via the NO/peroxynitrite and HOCl path.

To standard preparations for the induction of apoptosis the given concentrations of the single domain VHH fragments aCATcb0972 were added in the presence of 100 μM of the NOX1 inhibitor AEBSF, 50 mM of the HOCl scavenger taurine (TAU), 25 μM of the peroxynitrite scavenger FeTPPS or 2 mM of the singlet oxygen scavenger histidine (HIS). Control preparations were carried out parallel without inhibitors. After 3.5 hours at 37° C., 5% $CO_2$ the percentages of apoptotic cells were determined.

FIGS. 14A and 14B show that the single domain VHH fragment aCATcb0972 (binds to and inhibits catalase) induces apoptosis in the form of an optimum curve and a subsequent second increase. Here, apoptosis induction is inhibited by the NOX1 inhibitor AEBSF in the entire range of concentrations of the single domain VHH fragment. The HOCl scavenger taurine does not inhibit in the left range of concentrations of the optimum curve, but then results in a strong inhibition of the apoptosis in the entire further range of the optimum curve (FIG. 14A). The second increase of the apoptosis in the concentration range from 6.2 pg/ml of the single domain VHH fragment is not inhibited by taurine. The peroxynitrite scavenger FeTPPS only in the left part of the optimum curve results in a strong inhibition and then, changes the optimum curve of apoptosis induction into a plateau curve. The singlet oxygen scavenger histidine does not result in an inhibition of apoptosis, but changes the optimum curve into a plateau curve.

That is, FIGS. 14A and 14B proves that the apoptosis-inducing effect of the single domain VHH fragment aCATcb0972 actually is caused by the reactivation of the ROS signaling, since at all applied concentrations a complete inhibition of the apoptosis induction takes place when the superoxide anion production is inhibited by AEBSF. Moreover, the result proven in FIGS. 14A and B show that the optimum range of the apoptosis induction (0-6.2 pg/ml) is characterized by a succession of NO/peroxynitrite path and HOCl path. In the range of 0.09 and 0.18 pg/ml of aCATcb0972 there is an inhibition by the peroxynitrite scavenger FeTPPS, but not inhibition by the HOCl scavenger taurine, what indicates the course of the NO/peroxynitrite path. From 0.75 pg/ml of the Fab fragment there is no substantial inhibition by FeTPPS, but a very strong inhibition by taurine, what proves the course of the HOCl path. As expected, at 0.37 pg/ml both signal paths overlap. The new increase of the apoptosis induction at higher concentrations of the single domain VHH fragment depends
i) on the production of superoxide anions,
ii) on the degree of the catalase inhibition and neither is affected by the HOCl scavenger nor the peroxynitrite scavenger.

Accordingly, it is a sole effect of $H_2O_2$ and not that of the specific ROS signal path.

Figure 1:
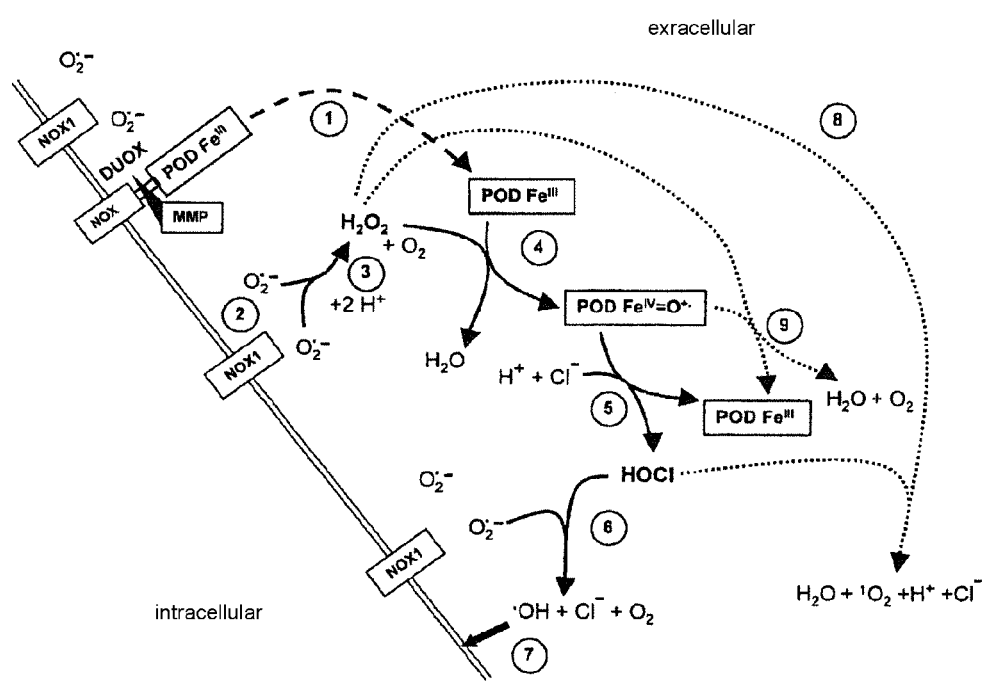
FIG. 1: Scheme 1 (HOCl signal path) shows the membrane of a malignant transformed cell characterized by expression of NOX1 and DUOX (consisting of an NOX1-related NOX domain and a peroxidase domain). Here, the expression of NOX1 represents a specific feature of malignant cells, whereas DUOX can also be detected in normal cells. By the effect of a matrix metalloprotease (MMP) the peroxidase domain is released ①. The superoxide anions ② generated by NOX1 dismutate to $H_2O_2$ ③ that is used by peroxidase as a substrate ④. Here, from the native peroxidase (PODFe$^{III}$) there is formed the reactive intermediate "Compound I" (PODFe$^{IV}$=O$^+$) that is able to oxidize chloride ions to HOCl ⑤. The HOCl present in the micromolar range of concentrations only develops a toxic effect if it reacts with superoxide anions to form apoptosis-inducing hydroxyl radicals ⑥. Here, the decisive step is the lipid peroxidation by hydroxyl radicals ⑦ that via the formation of ceramides results in the induction of the mitochondrial path of the apoptosis (not shown). If there is relative excess of $H_2O_2$ over peroxidase the reactions shown in ⑧ and ⑨ by consuming HOCl ⑧ or preventing its synthesis ⑨ may lead to the termination of the HOCl signal path.
Figure 2:
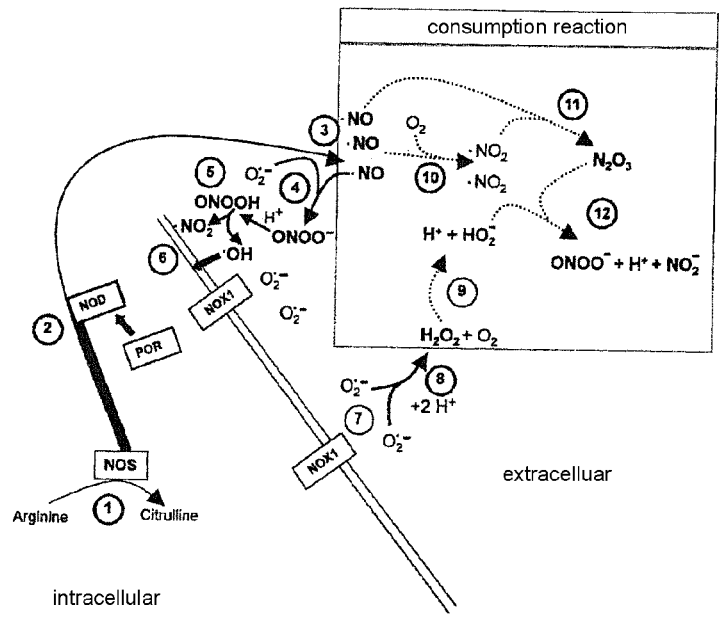
FIG. 2: Scheme 2 shows the NO/peroxynitrite signal path of transformed cells. NO Synthase (NOS) generates nitric oxide (NO) ①. A quite considerable part of the NO is converted by NO dioxygenase (NOD) to nitrate ②. Here, NOD is controlled by cytochrome P450-dependent oxidoreductase (POR). NO exhibits a high membrane permeability ③ and can react with superoxide anions generated on the outside of the transformed cells to peroxynitrite (ONOO$^-$) ④. The peroxynitrite acid (ONOOH) ⑤ formed by protonation of peroxynitrite extremely rapidly decomposes to $NO_2$ and apoptosis-inducing hydroxyl radicals ⑥. The reaction sequence ⑦-⑫ shows an alternative reaction option for NO that altogether represents a consumption reaction and can weaken or terminate the NO/peroxynitrite path. However, this consumption reaction represents an option to modulate $H_2O_2$-dependent processes by increasing the NO concentration.
Figure 3:
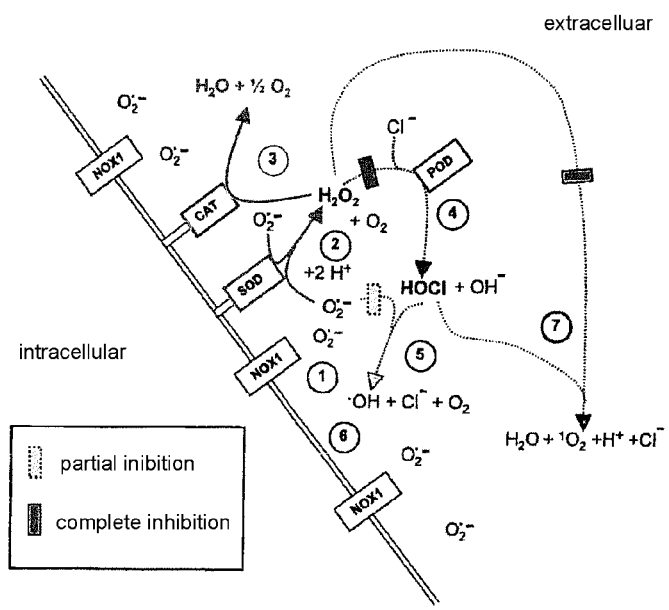
FIG. 3: Scheme 3 shows that tumor cells effectively suppress the HOCl signal path ①, ②, ④-⑥ by expression of membranous catalase (CAT) by preventing the HOCl synthesis by destroying $H_2O_2$ ③. Certainly, membranous SOD promotes the dismutation of superoxide anions to $H_2O_2$, what could influence the HOCl path, but this effect does not bring results by the effect of catalase that degrades said $H_2O_2$. However, the SOD-mediated decrease in the concentration of superoxide anions inhibits the interaction between HOCl and superoxide anions ⑤ that is essential for the signal path and in this way enhances the protection of the tumor cell from ROS signaling. The analysis of the inhibiting effects shows that the catalase on the membrane of tumor cells is sufficient for a complete and dominant inhibition of the HOCl synthesis, whereas certainly the SOD effect alone offers clearly measureable, but only partial protection.
Figure 4:
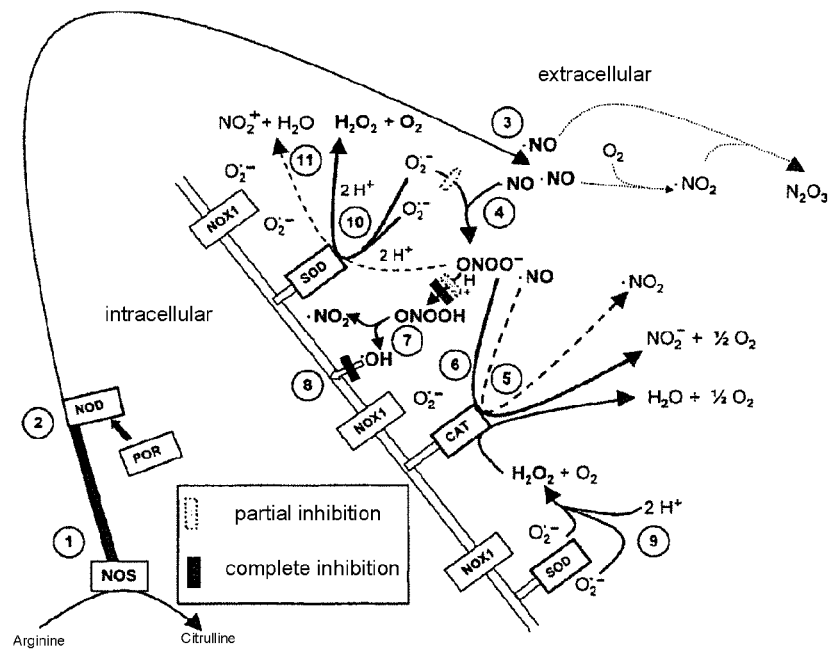
FIG. 4: Scheme 4 summarizes the complex interaction of membranous catalase and SOD in the protection of tumor cells from the NO/peroxynitrite signal path. Catalase prevents the formation of peroxynitrite by oxidation of NO to $NO_2$ ⑤ and destroys possibly forming peroxynitrite by degradation ⑥. SOD prevents the formation of peroxynitrite by scavenging superoxide anions ④ and also is able to destroy peroxynitrite ⑪ to a limited extent. It may also be speculated that the $H_2O_2$ formed by SOD in reaction ⑩ by the consumption reaction shown in scheme 2 contributes to an additional decrease in the NO concentration. The scheme impressively shows that tumor cells in a coordinated manner are capable to repeatedly control the NO/peroxynitrite path.

Changing the optimum curve of the apoptosis induction into a plateau curve by the singlet oxygen scavenger histidine and the peroxynitrite scavenger FeTPPS indicates that at concentrations of the single domain VHH fragment aCATcb0872>0.75 pg/ml also singlet oxygen seems to play a role. Singlet oxygen can result from the reaction of $H_2O_2$ with peroxynitrite. Singlet oxygen is also known to be able to inactivate catalase. Then, the increased availability of $H_2O_2$ caused thereby can cause the side reactions ⑧ and ⑨ shown in FIG. 1, whereby HOCl is consumed or less HOCl is synthesized. In this way, a drop of apoptosis induction on the right side of the optimum curve is caused.

Example 6 Specific Sensitization of Tumor Cells for Apoptosis-Inducing ROS Signaling by Single Domain VHH Fragments Against SOD The specific apoptosis induction in MKN-45 gastric carcinoma cells by single domain VHH fragments against SOD is shown in FIG. 15A. The percentage of apoptotic cells is plotted on the X axis.

MKN-45 cells under standard conditions for autocrine apoptosis induction were mixed with the given concentrations of single domain VHH fragments that bind to but do not inhibit human SOD1 (aSODcb0987, aSODcb0991) and single domain VHH fragments that bind to and inhibit human SOD (aSODcb0989) and were further incubated for 3.5 hours at 37° C., 5% $CO_2$. In parallel under the same conditions recombinant Fab fragments (consisting of a light and a heavy chain) were applied that are directed against and neutralize human catalase (Abd aSOD15660; FIG. 15B). Thereafter, the percentage of apoptotic cells (double preparations) was determined in accordance with the above-mentioned classical apoptosis criteria.

FIGS. 15A and 15B show that single domain VHH fragments that inhibit SOD, but not such that only bind to the enzyme, induce apoptosis in the tumor cells. Here, the effect is represented in the form of a broad optimum curve. An optimum curve of the apoptosis induction is also achieved by the classical Fab fragment AbD aSOD 15660 (FIG. 15B), however, for that, in order to achieve the same effect, there is required a concentration that is 250-fold higher in comparison to that of the single domain VHH fragment.

That is, FIGS. 15A and 15B shows that it is not sufficient for the sensitization that antibodies bind to SOD. The specific inhibition of the function of SOD seems to be essential for the sensitization. It is noteworthy that the specific inhibition of the membranous SOD is sufficient to reactivate the ROS signaling that results in the apoptosis. Noteworthy and unexpected is the finding that neutralizing single domain VHH fragments have a much stronger apoptosis-inducing effect than classical neutralizing Fab fragments. Due to the different structure of these two groups of fragments it would have been to be expected that the classical Fabs would have been to be applied with twice the concentration in comparison with single domain VHH fragments in order to achieve a similar effect. However, the difference is a factor of about 250.

FIGS. 16A and 16B show that the SOD-neutralizing single domain VHH fragment aSODcb0989 in gastric carcinoma cells of the MKN-45 line induces specific ROS signaling exclusively via the NO/peroxynitrite path.

To the standard preparations for the induction of apoptosis the given concentrations of the single domain VHH fragment aSODcb0989 were added in the presence of 100 μM of the NOX1 inhibitor AEBSF, 25 μM of the peroxynitrite scavenger FeTPPS, 50 mM of the HOCl scavenger taurine (TAU) or 2 mM of the singlet oxygen scavenger histidine (HIS). Control preparations were carried out parallel without inhibitors. After 3.5 hours at 37° C., 5% $CO_2$ the percentages of apoptotic cells were determined.

FIGS. 16A and 16B show that SOD-neutralizing single domain VHH fragments in gastric carcinoma cells of the MKN-45 line induce apoptosis in the form of a broad optimum curve which is followed by an indicated second increase. The apoptosis induction is inhibited by AEBSF in the entire concentration range. The entire optimum range is inhibited by FeTPPS, but not by taurine. Histidine results in a perceptible partial elimination of the drop of the right flank of the optimum curve.

That is, FIGS. 16A and 16B proves that apoptosis induced by aSODcb0989 in the tumor cells certainly is continuously induced via a superoxide anion-dependent process, but this (in contrast to aCATcb0972) exclusively is the NO/peroxynitrite path and HOCl signaling has no perceptible influence. This is also documented by the complete inhibition by means of FeTPPS and the disappearance of an inhibition by taurine. This result indicates that, given the absence of the SOD effect, obviously no sufficient $H_2O_2$ is available for the HOCl path. Since the NO/peroxynitrite path is very efficiently inhibited by membranous catalase it can be concluded from the result shown in FIGS. 16A and 16B that the inhibition of SOD by the single domain VHH fragment also must have resulted in an indirect inhibition of catalase. The different quality of the signal paths reactivated by aSODcb0989 and aCATcb0972 allows to exclude the theoretic assumption that the effect of aSODcb0989 could be a cross-reaction with catalase and thus also confirms the specificity of the effect of aSODcb0989.

Example 7: Relationship Between Single Domain VHH Fragments and Target Cells

FIGS. 17A and 17B show that single domain VHH fragments against catalase or SOD make different demands on the density of the target cells.

Preparations for the induction of apoptosis in addition to the standard cell density (12500 cells/100 μl) were also prepared with a lower cell density (4000 cells/100 μl) and increasing concentrations of the single domain VHH fragments aCATcb0972 or aSODcb0989 and incubated for four hours at 37° C., 5% $CO_2$. Thereafter, the percentages of apoptotic cells were determined.

FIG. 17A shows that apoptosis induction by the single domain VHH fragments directed against catalase only with higher density runs in an optimum manner, whereas in the application of the single domain VHH fragments directed against SOD there is much lesser attenuation of the effect when the target cells are present with a lower density (FIG. 17B). This difference gives evidence for the different quality of the reactivated signal paths and especially is consistent with the fact that an inhibition of SOD preferably reactivates the NO/peroxynitrite path, since this does not depend on a high cell density to the same extent as the HOCl-signal path.

Example 8: Synergistic Effect of Single Domain VHH Fragments Against Catalase and SOD FIGS. 18A and 18B show a noteworthy synergistic effect with the simultaneous application of single domain VHH fragments against catalase and SOD.

Standard preparations for the apoptosis induction with MKN-45 cells were mixed with increasing concentrations of the catalase-neutralizing single domain VHH fragment aCATcb0972 alone and in combination with 0.005 pg/ml of the SOD-neutralizing single domain VHH fragment aSODcb0989 or the single domain VHH fragment aSODcb0987 that binds to SOD but does not neutralize it (A). In the complementary experiment (B) mixing was done with increasing concentrations of aSODcb0989 alone or in combination with 0.005 pg/ml of the catalase-neutralizing single domain VHH fragment aCATcb0972. All preparations were incubated for 3.5 hours at 37° C., 5% $CO_2$. Thereafter, the percentages of apoptotic cells were determined.

Figure 18:
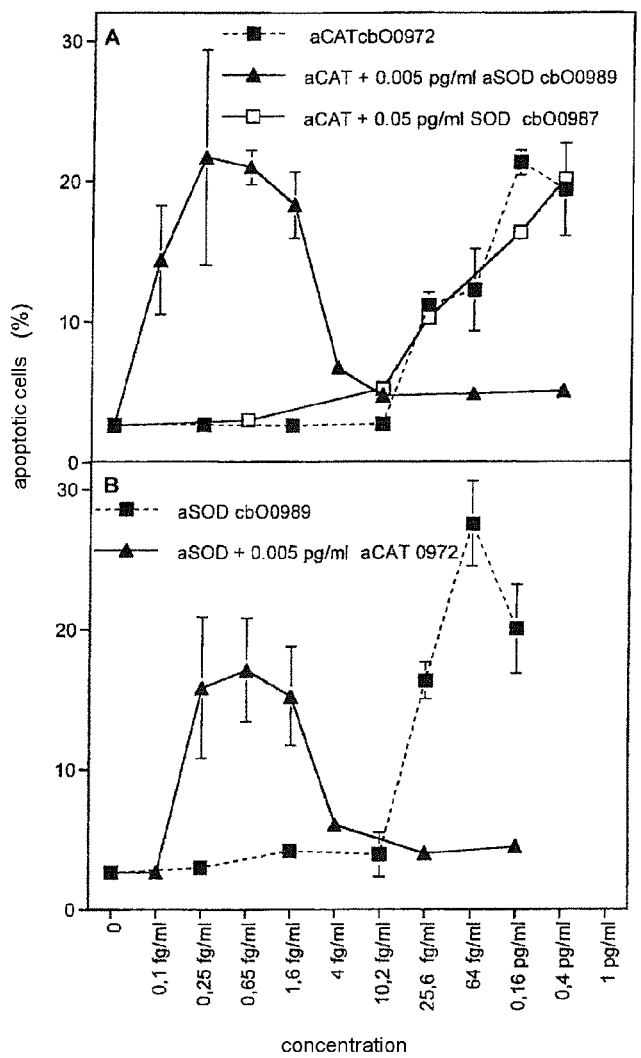

FIGS. 18A and 18B show that the concentration-dependent apoptosis-inducing effects already measured in the preliminary experiments can be confirmed both by aCATcb0972 (FIG. 18A) and aSODcb0989 (FIG. 18B). The combination with a minor concentration of the respectively complementary single domain VHH fragment that alone is not sufficient for the apoptosis induction (i.e. aSOD in increasing concentrations of aCAT and aCAT in increasing concentrations of aSOD) resulted in a noteworthy synergistic effect in the apoptosis induction. The specificity of said synergistic effect is proved by the fact that it has not appeared with the administration of a single domain VHH fragment that binds to but does not neutralize SOD (FIG. 18 A).

That is, FIG. 18 shows that the combination of single domain VHH fragments against catalase or SOD results in a very strong synergistic effect. When optimally using this effect the required concentrations of single domain VHH fragments could be drastically decreased.

Example 9: Synergistic Effect with Chemotherapeutic Agent

FIG. 19 shows that single domain VHH fragments neutralizing catalase or SOD, respectively, cause a strong synergistic effect with the established chemotherapeutic agent taxol.

Standard preparations for the apoptosis induction with MKN-45 cells were mixed with increasing concentrations of taxol alone or in combination with catalase-neutralizing aCATcb0972, SOD-neutralizing aSODcb0989 and SOD-binding but not neutralizing aSODcb0987 and incubated for 4 hours at 37° C., 5% $CO_2$. Thereafter, the percentages of apoptotic cells were determined.

FIG. 19 shows that taxol induces apoptosis in the tumor cells in a concentration-dependent manner.

Here, the optimum effect was found in the concentration range of 1100 ng/ml. This effect was to be expected. In combination with single domain VHH fragments that either could inhibit catalase or SOD the taxol-dependent optimum curve surprisingly was drastically displaced to a lower concentration range. Now, the optimum of the effect was between 0.17 ng/ml and 0.5 ng/ml. This impressive displacement of the required concentration to less than a thousandth could only be achieved by single domain VHH fragments that also neutralize the respective target structure (catalase or SOD), while a mere bond did not cause any enhancing effect.

The effect shown in FIG. 19 at first is of high interest because it proves a previously unknown functional connection between the effect of taxol on tumor cells and ROS signaling. The appearance of a synergistic effect with single domain VHH fragments against SOD or catalase offers the opportunity to conserve resources in all by suitably combining the active ingredients, to thereby obtain a reduction in costs of the therapy and also opens the chance to reduce or even avoid the side effects caused by taxol and to avoid possible side effects of the single domain VHH fragments.

Example 10: Specific Sensitization of Tumor Cells for Apoptosis-Inducing ROS Signaling by Hybrid Molecules from Catalase- or SOD-Neutralizing Single Domain VHH Fragments FIG. 20 shows that the synergistic effect between single domain VHH fragments aCAT and aSOD can be concentrated in one hybrid molecule.

Standard preparation for the apoptosis induction with MKN-45 cells were mixed with increasing concentrations of catalase-neutralizing aCATcb0972, SOD-neutralizing aSODcb0989, the hybrid molecules from aCATcb0972 and aSODcb0989 in the two possible arrangements as well as a neutralizing conventional monoclonal antibody against catalase (Sigma) as a control and incubated for 3.5 hours at 37° C., 5% $CO_2$. Thereafter, the percentages of apoptotic cells were determined.

FIG. 20 shows that the synergistic effect observed with the combination of the individually added single domain VHH fragments aCATcb0972 and aSODcb0989 can actually be concentrated in hybrid molecules. Here, the arrangement aCATaSOD seemed to be gradually superior over the reverse arrangement. While the optimum effect of the individually applied single domain VHH fragments was in the concentration range of about 170 fg/ml, the optimum effect by the hybrid molecules was already achieved at 0.24 fg/ml. These noteworthy activities are conflicted with a dramatically lower efficacy of the conventional monoclonal antibody that develops its optimum effect at 111 ng/ml. In the illustration the data for classical recombinant Fab fragments that neutralize SOD or catalase have not been included for sake of clarity. Their optimum efficacy is in the range of 0.1-0.3 ng/ml.

That is, FIG. 20 confirms that i) the efficacy of single domain VHH fragments unexpectedly is much larger than that of conventional monoclonal antibodies or conventional recombinant Fab fragments and ii) a further very clear increase in the efficacy can be achieved when hybrid molecules are generated from single domain VHH fragments.

Example 11

FIGS. 21A and 21B show that the hybrid molecule from the single domain VHH fragments aCATcb0972 and aSODcb0989 in gastric carcinoma cells of the MKN-45 line induces specific ROS signaling exclusively via the NO/peroxynitrite path.

To standard preparations for the induction of the apoptosis there were added the given concentrations of the hybrid molecule aCATaSOD in the presence of 100 μM of the NOX1 inhibitor AEBSF, 25 μM of the peroxynitrite scavenger FeTPPS, 50 mM of the HOCl scavenger taurine (TAU) or 2 mM of the singlet oxygen scavenger histidine (HIS). Control preparations were carried out parallel without inhibitors. After 3 hours at 37° C., 5% $CO_2$ the percentages of apoptotic cells were determined.

FIG. 21 confirms that the hybrid molecule aCATaSOD in the tumor cells induces apoptosis via the reactivation of the ROS signaling, because the process is completely prevented by the inhibition of the synthesis of superoxide anions by means of AEBSF. Further it is apparent that the apoptosis induction reactivated by the hybrid molecule is exclusively the NO/peroxynitrite path, since there is a complete inhibition by FeTPPS, but no inhibition by taurine. The singlet oxygen scavenger in turn has an attenuating effect on the right-side drop of the optimum curve. The dominance of the NO/peroxynitrite path was unexpected and unpredictable from the previous results.

Example 12

FIG. 22 by means of siRNA-based analysis confirms the specificity of the ROS signaling that is induced by the hybrid molecule and results in apoptosis.

MKN-45 cells were transfected with 24 nM siRNA that was directed against NOX1, iNOS2, caspase-9, FAS receptor or caspase-8. Control preparations were transfected with irrelevant control siRNA. After 24 hours at 37° C. the cells were taken up in fresh medium and mixed with the given concentrations of the hybrid molecule aCATaSOD. The percentage of apoptotic cells is determined after four hours.

FIG. 22 shows that the apoptosis induction in the form of an optimum curve caused by the hybrid molecule aCATaSOD can only take place when intact NADPH oxidase (NOX1), NO synthase (iNOS2) and caspase-9 that is essential for the course of apoptosis via the mitochondrial path are available. The siRNA-mediated knockdown of these enzymes each completely prevents the apoptosis induction induced by the hybrid molecule and thus, proves the underlying ROS signaling via the NO/peroxynitrite path with subsequent mitochondrial apoptosis signaling. On the other hand, apoptosis induction by the hybrid molecule does not require the FAS receptor and its downstream caspase-8, what emphasizes the exclusive effect of the mitochondrial apoptosis path and excludes that the apoptosis path via the death receptor APO/FAS for the apoptosis induction under the selected conditions plays a role. However, the knockdown of the FAS receptor and caspase-8 prevents the supra-optimum drop of the apoptosis induction curve. This can be explained by the participation of FAS receptor and caspase-8 and singlet oxygen-related processes, as stated in Bauer, 2012 and coincides with the finding regarding histidine established in FIG. 21B.

From FIGS. 13A, 13B, 15A, 15B and 20, there were determined the concentrations of the antibodies and single domain VHH fragments that were necessary for an optimum apoptosis induction in the tumor cells (table 1). This table explains the superior efficacy of the single domain VHH fragments in comparison to classical recombinant Fab fragments and monoclonal antibodies. Table 2 emphasizes the impressive synergistic effect that can be achieved by the use of the hybrid molecules. The superior effect of the single domain VHH fragments over classical recombinant Fab fragments was not predictable and thus, unexpected. Rather, due to the current state of knowledge it was to be expected that neutralizing classical Fab fragments and neutralizing single domain VHH fragments when considering the molar concentration should achieve the same effect on the apoptosis induction, when considering the concentrations (pg/ml) thereby only a difference by factor 2 should have to be achieved. This non-predictable dramatic difference in the efficacy is surprising. This effect is best suited for the therapeutic use.

TABLE 1

| Antibody | optimum conc. | relation to opt. conc. single domain Fab | relation (molar basis) |
|---|---|---|---|
| aCAT cb0972 (single domain VHH) | 0.4 pg/ml | | |
| AbD aCAT 15562 (recomb. Fab classical) | 0.2 ng/ml | 500 | 250 |
| monoclonal aCAT (Sigma) | 111 ng/ml | 277 500 | 46 250 |
| aSOD cb0989 (single domain VHH) | 1.2 pg/ml | | |
| AbD aSOD 15660 | 0.3 ng/ml | 250 | 125 |

TABLE 2

| Antibody | optimum conc. | relation to opt. conc. hybrid Fab | relation (molar basis) |
|---|---|---|---|
| aCATaSOD (hybrid single dom. VHH) | 0.24 fg/ml | | |
| aCAT cb0972 (single domain VHH) | 0.17 pg/ml | 708 | 1416 |
| monoclonal aCAT (Sigma) | 111 ng/ml | $4.6 \times 10^8$ | $1.54 \times 10^8$ |
| aSOD cb0989 (single domain VHH) | 0.35 pg/ml | 1458 | 2916 |

The values were taken from FIGS. 13A, 13B, 15A, 15B, and 20. First it was determined by which amount the concentration of conventional recombinant Fab fragments and monoclonal antibodies has to be higher to achieve the same effect as with recombinant single domain VHH fragments. By including the molar masses of the various Fab fragments and antibodies then the relation was determined on the basis of molarities. In this correction there was employed the valid assumption that classical Fab fragments make up a third of the molar mass of a complete IgG molecule and that the molar mass of a single domain VHH fragment makes up approximately half the molar mass of a classical Fab fragment.

Example 13: Effect of Single Domain VHH Fragments with Catalase- or SOD-neutralizing Effect on Human Tumor Cells that are Only Capable to Establish the NO/Peroxynitrite Path While the human gastric carcinoma line MKN-45 used in the previous examples is characterized in that it can express the whole spectrum of the known intracellular ROS signaling (HOCl and NO/peroxynitrite path as main paths, nitryl chloride path as secondary path) when its membranous catalase is inhibited, in a series of other human tumor cell lines there is shown a limitation to the NO/peroxynitrite path (Heinzelmann and Bauer, 2010; Bauer, 2012). So, in the previous examinations it was found that a certain type of tumor each shows a uniform ROS signal system. A restriction to the NO/peroxynitrite signaling we so far only observed with neuroblastoma, Ewing's sarcoma, mammary carcinoma, ovarian carcinoma and small-cell lung carcinoma.

Figure 23:
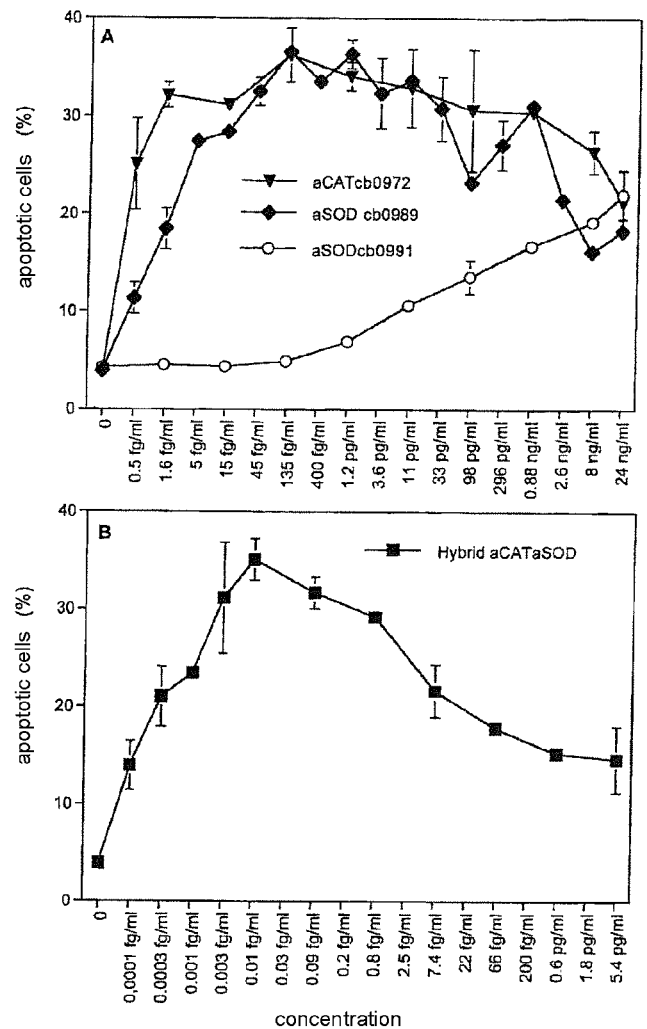

FIG. 23 shows that single domain VHH fragments can also reactivate apoptosis in tumor cells that can only form NO/peroxynitrite signaling.

10 000 cells of the human neuroblastoma line SHEP per 100 μl medium were mixed with the given concentrations of the catalase-neutralizing single domain VHH fragment aCATcb0972, the SOD-neutralizing single domain VHH fragment aSOD0989, the SOD-binding but not neutralizing single domain VHH fragment aSODcb991 and the hybrid molecule aCATaSOD and incubated for 5 hours at 37° C., 5% $CO_2$, before percentages of apoptotic cells were determined.

FIG. 23 shows that the catalase- and SOD-neutralizing single domain VHH fragments as well as the hybrid molecule aCATaSOD can induce concentration-dependent apoptosis in the neuroblastoma line SHEP. As expected, here the hybrid molecule proved to be much more effective than the single domain VHH fragments that each are only directed against one target structure. The SOD-binding but not neutralizing single domain VHH fragment aSODcb0991 at high concentrations also achieves an apoptosis-inducing effect, but for that there is required a $10^6$-fold higher concentration than for the neutralizing single domain VHH fragment.

That is, FIG. 23 confirms that also cell lines that after catalase inhibition are only capable for NO/peroxynitrite signaling can be brought into apoptosis by single domain VHH fragments directed against catalase or SOD. Also, here the synergistic effect between aCAT and aSOD appears. Noteworthy is the concentration-effect curve observed with this cell line that in comparison with the MKN-45 cell line only has a very flat long-lasting supra-optimum drop on the right flank.

The weak but significant apoptosis induction that is achieved by the single domain VHH fragment aSODcb0991 that can only bind but not neutralize can be explained best by the fact that after bonding of the single domain VHH fragment there is an internalization of the SOD and thus, its concentration on the surface is reduced, what should result in an effect analogous to the inhibition.

FIG. 24 shows that the effect of aSODcb0989 on SHEP cells can be further optimized when there is additionally employed the NO donor SNP.

10 000 cells of the human neuroblastoma line SHEP per 100 µl medium were mixed with the given concentrations of the SOD-neutralizing single domain VHH fragment aSOD0989. Parallel preparations received 20 µM or 100 µM of the NO donor sodium nitroprusside or were incubated without a further additive. After 5 hours at 37° C., 5% $CO_2$ the percentages of apoptotic cells were determined.

FIG. 24 shows that the additional administration of the NO donor (that alone is not able to induce apoptosis) both results in a sensitization concerning the reactivation of the apoptosis induction and effectively counteracts the supraoptimum right-side drop of the optimum curve. From this, modulation methods should be established that transform the optimum curve of the apoptosis induction into a plateau curve, what should result in a greater certainty of the therapeutic use.

Example 14: Single Domain VHH Fragments Exclusively Inhibit Membranous Catalase (that is Characteristic and Essential for Tumor Cells) and do not Achieve Intracellular Catalase (that Also Plays a Role in Normal Cells)

FIGS. 25A, 25B, 26A and 26B show that catalase-neutralizing single domain VHH fragments only neutralize the membranous catalase of tumor cells and cannot influence the intracellular catalase of normal cells.

6000 non-transformed 208F cells, transformed 208Fsrc3 cells, and MKN-45 tumor cells, respectively, each were seeded in 100 µl medium and mixed with 0.1 or 1 pg/ml catalase-neutralizing aCATcb0972 or only catalase-binding aCATcb0973. Control preparations were left without single domain VHH fragments. Subsequently, the indicated concentrations of glucose oxidase were added and apoptosis induction was measured after 1.5 hours. Glucose oxidase (GOX) generates $H_2O_2$ which is cell-permeable and thus, can be degraded both by intracellular and membranous catalase. At a sufficient concentration $H_2O_2$ induces apoptosis without selectivity with respect to the malignant status of cells (Ivanovas et al., Selective and nonselective apoptosis induction in transformed and nontransformed fibroblasts by exogenous reactive oxygen and nitrogen species. Anticancer Research, Anticancer Res. 22:841-856, 2002).

FIG. 25A shows that the tumor cell line MKN-45 is much better protected from $H_2O_2$ than the normal cells and the transformed cell line. In the presence of catalase-neutralizing single domain VHH fragments the tumor cells are very clearly sensitized for the effect of $H_2O_2$, whereas single domain VHH fragments that only bind to catalase do not result in a sensitization (FIG. 25B). FIGS. 26A and 26B show that the neutralizing single domain VHH fragments caused a sensitizing effect on the transformed line that however could not influence normal cells.

FIGS. 25A, 25B, 26A and 26B confirm the specific effect of the single domain VHH fragments on the malignant cells, whereas the normal cells are not influenced. Here, the greatest effect was observed with the tumor cells, since these, above all are protected by membranous catalase. Transformed cells are known to bear detectable amounts of catalase on the surface, that however is present in a lower local concentration than in tumor cells and thus, is not sufficient for the protection from ROS signaling. The lack of reaction in the normal cells proves that the single domain VHH fragments do not penetrate the cell and cannot influence the catalase that is present there. That is, they act specifically on the membranous catalase, as is especially characteristic for tumor cells. However, this very important statement about the reaction site of the single domain VHH fragments is only significant if at the same time it can be proved that an inhibition of the intracellular catalase of normal cells actually would have had influence on their sensitivity against $H_2O_2$.

With this control aspect is dealt in FIG. 27.

FIG. 27A-27F shows that the siRNA-mediated knockdown of the intracellular catalase of normal cells increases their sensitivity against $H_2O_2$.

Normal cells (208F), transformed cells (208Fsrc3) and tumor cells (MKN-45) were transfected with control siRNA (siCo) and siRNA against catalase (siCAT) and kept for 24 hours at 37° C. and 5% $CO_2$. Thereafter, the cells were taken up into fresh medium and taken up in a cell density of 6000 cells/100 µl medium. Subsequently, the preparations were treated either with increasing concentrations of GOX (27A-27C) or peroxynitrite (PON) (27D-27F). After 1.5 hours of incubation and 37° C. and 5% $CO_2$ the percentages of apoptotic cells were determined. To assess this experiment, it has to be recapitulated that GOX generates $H_2O_2$ that has a very good cell-permeability and thus, can be degraded both by membranous and intracellular catalase. On the other hand, exogenously added peroxynitrite reacts with the cell membrane when it contacts the cell. Thus, protection from the effect of peroxynitrite can only be achieved by catalase sitting on the outside of the membrane.

At first, FIG. 27A-27F confirm that tumor cells are much better protected from $H_2O_2$ and peroxynitrite than normal or transformed cells. Further, the figure shows that a siRNA-mediated degradation of catalase results in a very strong sensitization of normal cells, transformed cells, and tumor cells against the effect of $H_2O_2$. After treatment with peroxynitrite there appeared a completely different picture: now, the siRNA-mediated degradation of catalase in the normal cells does not result in a sensitization, whereas in the transformed cells and tumor cells there is a strong sensitization. This shows that only on the surface of the malignant cells, i.e. the transformed and tumor cells, there is catalase that protects from exogenous peroxynitrite. A protective membranous catalase effect cannot be detected in the normal cells. The finding made by means of $H_2O_2$-generating GOX shows that normal cells possess functional protective catalase the effect of which can be detected e.g. by a siRNA-mediated knockdown. Since in the experiment shown in FIGS. 26A and 26 B however a sensitization of normal cells against $H_2O_2$ cannot be detected by means of catalase-neutralizing single domain VHH fragments it is proved that they could not act inside the cell.

Example 15: The In Vitro Effect Shown for Single Domain VHH Fragments Correlates with an Inhibition of the Tumor Growth In Vivo FIGS. 28A, 28B and 29 show that the growth of a human colon carcinoma xenotransplant on immunocompromised mice is inhibited by the repeated administration of the single domain VHH fragment aSODcb0989.

The experiments carried out in FIGS. 28A and 28B and FIG. 29 were carried out by a commercial certified supplier (Oncotest GmbH, Freiburg). Here, xenotransplants of a human colon carcinoma were implanted in suitable mice. After the tumors had grown on and a certain minimum size had been achieved, the therapeutic test was started. aSODcb0989 in the indicated doses (mg/kg body weight) or buffer were intravenously applied twice a week. Also, the tumor sizes were measured twice a week by means of a caliber.

At first, FIGS. 28A and 28B show that the tumor growth in the control animals is characterized by a very clear spread. When applying 0.03 mg/kg of aSODcb0989 there does not result a recognizable difference to the controls (FIG. 28A). When administering 0.3 mg/kg of aSODcb0989 the group treated with the single domain VHH fragment very clearly differs from the control group, even though both groups underlie a very strong spread. The illustrated difference in the tumor volume between the control group and treated group is the expression of a clear proliferation inhibition by aSODcb0989. When further increasing the dose of aSODcb0989 to 0.9 mg/kg (FIG. 29) in some animals the growth inhibition is enhanced, whereas in other animals there is caused the contrary. This shows that also in vivo a dose-effect curve in the form of an optimum is present and the conditions in the experiment shown in FIG. 29 have reached the limit of the concentration for the supra-optimum inhibition.

The invention claimed is:

1. A composition formulated for the induction of tumor cell apoptosis, said composition comprising an amount of either (a) a single domain VHH fragment effective to specifically bind to and inhibit superoxide dismutase 1 (SOD1) or (b) a bispecific hybrid single domain VHH fragment effective to specifically bind to and inhibit both catalase (CAT) and superoxide dismutase 1 (SOD1), characterized in that said single domain VHH fragment contains a combination of three CDR sequences (CDR1, CDR2, and CDR3) specific and said bispecific hybrid single domain VHH fragment contains a combination of six CDR sequences specific to either cb 1081 or cb 1082.

2. The composition according to claim 1, wherein said composition comprises said single domain VHH fragment and said single domain VHH fragment contains a combination of a CDR1 sequence comprising SEQ ID NO: 34, a CDR2 sequence comprising SEQ ID NO: 35, and a CDR3 sequence comprising SEQ ID NO: 36.

3. The composition according to claim 2, wherein said the amino acid sequence of said single domain VHH fragment is set forth in SEQ ID NO: 15.

4. The composition according to claim 2, wherein said single domain VHH fragment is cb 0989.

5. The composition according to claim 1, wherein said composition comprises said bispecific hybrid single domain VHH fragment and the amino acid sequence of said bispecific hybrid single domain VHH fragment is selected from the group consisting of SEQ ID NO: 17 and SEQ ID NO: 18.

6. The composition according to claim 1, wherein said either single domain VHH fragment or bispecific hybrid single domain VHH fragment further includes a marker.

7. The composition according to claim 1, wherein said either single domain VHH fragment or bispecific hybrid single domain VHH fragment is connected to a cytotoxic agent.

8. The composition according to claim 1, wherein said either single domain VHH fragment or bispecific hybrid single domain VHH fragment is connected to one or more polyethylene glycol molecules to form a complex that exhibits a prolonged retention time in a target organism as compared to said either single domain VHH fragment or bispecific hybrid single domain VHH fragment alone.

9. A pharmaceutical composition comprising the composition according to claim 1 in combination with a tumor therapeutic agent.

10. The pharmaceutical composition according to claim 9, wherein said tumor therapeutic agent is taxol.

* * * * *

SEQUENCE LISTING

```
<160> NUMBER OF SEQ ID NOS: 51

<210> SEQ ID NO 1
<211> LENGTH: 19
<212> TYPE: RNA
<213> ORGANISM: artificial sequence
<220> FEATURE:
<223> OTHER INFORMATION: control siRNA

<400> SEQUENCE: 1
uucuccgaac gugucacgu                                                  19

<210> SEQ ID NO 2
<211> LENGTH: 19
<212> TYPE: RNA
<213> ORGANISM: artificial sequence
<220> FEATURE:
<223> OTHER INFORMATION: control siRNA antisense

<400> SEQUENCE: 2
acgugacacg uucggagaa                                                  19

<210> SEQ ID NO 3
<211> LENGTH: 21
<212> TYPE: DNA
<213> ORGANISM: artificial sequence
<220> FEATURE:
<223> OTHER INFORMATION: si RNA fasr

<400> SEQUENCE: 3
aaggagtaca cagacaaagc c                                               21

<210> SEQ ID NO 4
<211> LENGTH: 21
<212> TYPE: DNA
<213> ORGANISM: artificial sequence
<220> FEATURE:
<223> OTHER INFORMATION: siRNA casp 8

<400> SEQUENCE: 4
aagagtctgt gcccaaatca a                                               21

<210> SEQ ID NO 5
<211> LENGTH: 21
<212> TYPE: DNA
<213> ORGANISM: artificial sequence
<220> FEATURE:
<223> OTHER INFORMATION: siRNA casp 9

<400> SEQUENCE: 5
cagtgacatc tttgtgtcct a                                               21
```

<210> SEQ ID NO 6
<211> LENGTH: 21
<212> TYPE: DNA
<213> ORGANISM: artificial sequence
<220> FEATURE:
<223> OTHER INFORMATION: siRNA NOX

<400> SEQUENCE: 6
ccgacaaata ctactacaca a          21

<210> SEQ ID NO 7
<211> LENGTH: 21
<212> TYPE: DNA
<213> ORGANISM: artificial sequence
<220> FEATURE:
<223> OTHER INFORMATION: siRNA NOS2

<400> SEQUENCE: 7
ctgggccgtg caaaccttca a          21

<210> SEQ ID NO 8
<211> LENGTH: 21
<212> TYPE: DNA
<213> ORGANISM: artificial sequence
<220> FEATURE:
<223> OTHER INFORMATION: siRNA cat

<400> SEQUENCE: 8
ccggatctca cttggcggca a          21

<210> SEQ ID NO 9
<211> LENGTH: 21
<212> TYPE: DNA
<213> ORGANISM: artificial sequence
<220> FEATURE:
<223> OTHER INFORMATION: siRNA mouse cat

<400> SEQUENCE: 9
cccaatagga gataaactta a          21

<210> SEQ ID NO 10
<211> LENGTH: 128
<212> TYPE: PRT
<213> ORGANISM: artificial sequence
<220> FEATURE:
<223> OTHER INFORMATION: catalase binding

<400> SEQUENCE: 10

Met Ala Gln Val Gln Leu Val Glu Ser Gly Gly Gly Leu Val Gln Ala
1               5                   10                  15

Gly Gly Ser Leu Arg Leu Ser Cys Ala Ala Ser Glu Arg Thr Phe Asn
            20                  25                  30

Thr Tyr Gly Met Gly Trp Phe Arg Gln Ala Pro Gly Lys Glu Arg Glu
        35                  40                  45

Phe Val Ala Thr Ile Ser Trp Ser Gly Asp Ser Thr Tyr Tyr Ala Asp
    50                  55                  60

Ser Val Lys Gly Arg Phe Thr Ile Ser Arg Asp Asn Ala Lys Asn Thr
65                  70                  75                  80

Met Tyr Leu Gln Met Asn Ser Leu Lys Pro Glu Asp Thr Ala Val Tyr
                85                  90                  95

Tyr Cys Asn Ala Asn Ser Glu Tyr Gly Asp Ser Tyr Trp Gly Gln Gly
            100                 105                 110

```
Thr Gln Val Thr Val Ser Ser Lys Lys Lys His His His His His
        115                 120                 125

<210> SEQ ID NO 11
<211> LENGTH: 128
<212> TYPE: PRT
<213> ORGANISM: artificial sequence
<220> FEATURE:
<223> OTHER INFORMATION: catalase binding

<400> SEQUENCE: 11

Met Ala Glu Val Gln Leu Val Glu Ser Gly Gly Gly Leu Val Gln Pro
1               5                   10                  15

Gly Gly Ser Leu Arg Leu Ser Cys Ala Val Ser Gly Phe Ile Phe Asn
            20                  25                  30

Thr Tyr Ser Met Arg Trp Gly Arg Gln Ala Pro Gly Lys Gly Leu Glu
        35                  40                  45

Trp Val Ser Ser Ile Ser Thr Gly Gly Tyr Ser Thr Tyr Ala Asp Ser
    50                  55                  60

Val Lys Gly Arg Phe Thr Ile Ser Arg Asp Asn Ala Lys Asn Leu Val
65                  70                  75                  80

Tyr Leu Gln Met Asn Ser Leu Lys Pro Glu Asp Thr Ala Val Tyr Tyr
                85                  90                  95

Cys Gly Trp Gly Ala Phe Val Arg Gly Glu Arg Pro Gln Gly Gln Gly
            100                 105                 110

Thr Gln Val Thr Val Ser Ser Lys Lys Lys His His His His His
        115                 120                 125

<210> SEQ ID NO 12
<211> LENGTH: 133
<212> TYPE: PRT
<213> ORGANISM: artificial sequence
<220> FEATURE:
<223> OTHER INFORMATION: catalase binding

<400> SEQUENCE: 12

Met Ala Gln Val Gln Leu Val Glu Ser Gly Gly Gly Leu Val Gln Pro
1               5                   10                  15

Gly Gly Ser Leu Arg Leu Ser Cys Ala Ala Ser Gly Ser Ile Phe Ser
            20                  25                  30

Ile Ala Ser Met Gly Trp Tyr Arg Gln Ala Pro Gly Lys Gln Arg Asp
        35                  40                  45

Leu Val Ala Thr Ile Thr Ser Asp Gly Ser Thr Lys Tyr Ala Asp Ser
    50                  55                  60

Val Lys Gly Arg Phe Thr Ile Ser Arg Asp Asn Ala Lys Asn Thr Met
65                  70                  75                  80

Tyr Leu Gln Met Asn Ser Val Lys Pro Glu Asp Ala Ala Val Tyr Tyr
                85                  90                  95

Cys Asn Ala Asp Ala Asp Asp Leu Glu Pro Gly Ser Tyr Asp Tyr Asp
            100                 105                 110

Tyr Trp Gly Gln Gly Thr Gln Val Thr Val Ser Ser Lys Lys Lys His
        115                 120                 125

His His His His His
        130

<210> SEQ ID NO 13
<211> LENGTH: 133
<212> TYPE: PRT
```

<213> ORGANISM: artificial sequence
<220> FEATURE:
<223> OTHER INFORMATION: catalase binding

<400> SEQUENCE: 13

Met Ala Gln Val Gln Leu Val Glu Ser Gly Gly Gly Leu Val Gln Pro
1               5                   10                  15

Gly Gly Ser Leu Arg Leu Ser Cys Ala Ala Ser Ala Ser Ile Phe Ser
            20                  25                  30

Ile Tyr Val Met Ala Trp Tyr Arg Gln Ala Pro Gly Lys Gln Arg Glu
        35                  40                  45

Leu Val Ala Thr Val Thr Ser Gly Gly Ala Thr Asn Tyr Ala Asn Ser
    50                  55                  60

Val Lys Gly Arg Phe Thr Ile Ser Arg Asp Asn Ala Lys Asn Thr Met
65                  70                  75                  80

Asp Leu Gln Met Asn Ser Leu Lys Pro Glu Asp Thr Ala Val Tyr Tyr
                85                  90                  95

Cys Asn Ala Glu Asp Tyr Asp Tyr Gly Leu Ser Arg Ser Lys Ile
            100                 105                 110

Tyr Trp Gly Gln Gly Thr Gln Val Thr Val Ser Ser Lys Lys Lys His
        115                 120                 125

His His His His His
        130

<210> SEQ ID NO 14
<211> LENGTH: 127
<212> TYPE: PRT
<213> ORGANISM: artificial sequence
<220> FEATURE:
<223> OTHER INFORMATION: SOD binding

<400> SEQUENCE: 14

Met Ala Gln Val Gln Leu Val Glu Ser Gly Gly Gly Ile Val Gln Pro
1               5                   10                  15

Gly Gly Ser Leu Arg Leu Ser Cys Val Ala Ser Glu Ser Ile Ser Glu
            20                  25                  30

Ile Asp Ala Met Tyr Trp His Arg Gln Ala Pro Gly Lys Glu Arg Glu
        35                  40                  45

Leu Val Ala Gly Ile Thr Asn Asp Gly Thr Arg Tyr Tyr Ala Asp Ser
    50                  55                  60

Val Lys Gly Arg Phe Thr Ile Ser Arg Asp Asn Ala Lys Ser Thr Leu
65                  70                  75                  80

Tyr Leu Gln Met Asn Ser Leu Lys Phe Glu Asp Thr Ala Met Tyr Tyr
                85                  90                  95

Cys Ala Ala Leu Pro Asn Pro Pro Pro Gly Tyr Trp Gly Gln Gly Thr
            100                 105                 110

Gln Val Thr Val Ser Ser Lys Lys Lys His His His His His
        115                 120                 125

<210> SEQ ID NO 15
<211> LENGTH: 127
<212> TYPE: PRT
<213> ORGANISM: artificial sequence
<220> FEATURE:
<223> OTHER INFORMATION: SOD binding

<400> SEQUENCE: 15

Met Ala Gln Val Gln Leu Val Glu Ser Gly Gly Gly Leu Val Gln Ser
1               5                   10                  15

Gly Gly Ser Leu Thr Leu Ser Cys Thr Ala Ser Gly Phe Thr Ile Ser
            20                  25                  30

Asn Tyr Pro Met Thr Trp Val Arg Gln Ala Pro Gly Lys Gly Leu Glu
        35                  40                  45

Trp Val Ser Arg Ile Asn Ser Gly Gly Asp Arg Thr Leu Tyr Ala Asp
50                  55                  60

Ser Val Lys Gly Arg Phe Thr Val Ser Arg Asp Asn Ala Arg Asn Thr
65                  70                  75                  80

Met Tyr Leu Gln Met Asn Asn Leu Lys Pro Glu Asp Thr Gly Leu Tyr
                85                  90                  95

Phe Cys Ala Asp Ser Gly Ala Gly Trp Arg Tyr Trp Gly Gln Gly Thr
            100                 105                 110

Gln Val Thr Val Ser Ser Lys Lys Lys His His His His His His
            115                 120                 125

<210> SEQ ID NO 16
<211> LENGTH: 127
<212> TYPE: PRT
<213> ORGANISM: artificial sequence
<220> FEATURE:
<223> OTHER INFORMATION: SOD binding

<400> SEQUENCE: 16

Met Ala Gln Val Gln Leu Val Glu Ser Gly Gly Gly Ile Val Gln Pro
1               5                   10                  15

Gly Gly Ser Leu Arg Leu Ser Cys Val Ala Ser Glu Ser Ile Ser Asp
            20                  25                  30

Ile Asp Ala Met Tyr Trp His Arg Gln Ala Pro Gly Lys Arg Arg Glu
        35                  40                  45

Leu Val Ala Gly Ile Thr Asn Asp Gly Thr Glu Tyr Phe Ala Asp Ser
50                  55                  60

Val Lys Gly Arg Phe Ala Ile Ser Arg Asp Asn Thr Lys Ser Ser Leu
65                  70                  75                  80

Tyr Leu Gln Met Asn Ser Leu Lys Leu Glu Asp Thr Ala Met Tyr Tyr
                85                  90                  95

Cys Ala Thr Leu Pro Asn Pro Pro Gly Tyr Trp Gly Gln Gly Thr
            100                 105                 110

Gln Val Thr Val Ser Ser Lys Lys Lys His His His His His His
            115                 120                 125

<210> SEQ ID NO 17
<211> LENGTH: 260
<212> TYPE: PRT
<213> ORGANISM: artificial sequence
<220> FEATURE:
<223> OTHER INFORMATION: bispecific

<400> SEQUENCE: 17

Met Ala Gln Val Gln Leu Val Glu Ser Gly Gly Gly Leu Val Gln Ala
1               5                   10                  15

Gly Gly Ser Leu Arg Leu Ser Cys Ala Ala Ser Glu Arg Thr Phe Asn
            20                  25                  30

Thr Tyr Gly Met Gly Trp Phe Arg Gln Ala Pro Gly Lys Glu Arg Glu
        35                  40                  45

Phe Val Ala Thr Ile Ser Trp Ser Gly Asp Ser Thr Tyr Tyr Ala Asp
50                  55                  60

Ser Val Lys Gly Arg Phe Thr Ile Ser Arg Asp Asn Ala Lys Asn Thr

```
                65                  70                  75                  80
Met Tyr Leu Gln Met Asn Ser Leu Lys Pro Glu Asp Thr Ala Val Tyr
                    85                  90                  95

Tyr Cys Asn Ala Asn Ser Glu Tyr Gly Asp Ser Tyr Trp Gly Gln Gly
                100                 105                 110

Thr Gln Val Thr Val Ser Ser Gly Gly Gly Ser Gly Gly Gly Gly
                115                 120                 125

Ser Gly Gly Gly Ser Ala Gln Val Gln Leu Val Glu Ser Gly Gly
            130                 135                 140

Gly Leu Val Gln Ser Gly Gly Ser Leu Thr Leu Ser Cys Thr Ala Ser
145                 150                 155                 160

Gly Phe Thr Ile Ser Asn Tyr Pro Met Thr Trp Val Arg Gln Ala Pro
                165                 170                 175

Gly Lys Gly Leu Glu Trp Val Ser Arg Ile Asn Ser Gly Gly Asp Arg
                180                 185                 190

Thr Leu Tyr Ala Asp Ser Val Lys Gly Arg Phe Thr Val Ser Arg Asp
                195                 200                 205

Asn Ala Arg Asn Thr Met Tyr Leu Gln Met Asn Asn Leu Lys Pro Glu
            210                 215                 220

Asp Thr Gly Leu Tyr Phe Cys Ala Asp Ser Gly Ala Gly Trp Arg Tyr
225                 230                 235                 240

Trp Gly Gln Gly Thr Gln Val Thr Val Ser Ser Lys Lys Lys His His
                245                 250                 255

His His His His
        260

<210> SEQ ID NO 18
<211> LENGTH: 260
<212> TYPE: PRT
<213> ORGANISM: artificial sequence
<220> FEATURE:
<223> OTHER INFORMATION: bispecific

<400> SEQUENCE: 18

Met Ala Gln Val Gln Leu Val Glu Ser Gly Gly Gly Leu Val Gln Ser
1               5                   10                  15

Gly Gly Ser Leu Thr Leu Ser Cys Thr Ala Ser Gly Phe Thr Ile Ser
            20                  25                  30

Asn Tyr Pro Met Thr Trp Val Arg Gln Ala Pro Gly Lys Gly Leu Glu
                35                  40                  45

Trp Val Ser Arg Ile Asn Ser Gly Gly Asp Arg Thr Leu Tyr Ala Asp
        50                  55                  60

Ser Val Lys Gly Arg Phe Thr Val Ser Arg Asp Asn Ala Arg Asn Thr
65                  70                  75                  80

Met Tyr Leu Gln Met Asn Asn Leu Lys Pro Glu Asp Thr Gly Leu Tyr
                85                  90                  95

Phe Cys Ala Asp Ser Gly Ala Gly Trp Arg Tyr Trp Gly Gln Gly Thr
                100                 105                 110

Gln Val Thr Val Ser Ser Gly Gly Gly Gly Ser Gly Gly Gly Gly Ser
                115                 120                 125

Gly Gly Gly Gly Ser Ala Gln Val Gln Leu Val Glu Ser Gly Gly Gly
            130                 135                 140

Leu Val Gln Ala Gly Gly Ser Leu Arg Leu Ser Cys Ala Ala Ser Glu
145                 150                 155                 160

Arg Thr Phe Asn Thr Tyr Gly Met Gly Trp Phe Arg Gln Ala Pro Gly
```

```
                165                 170                 175
Lys Glu Arg Glu Phe Val Ala Thr Ile Ser Trp Ser Gly Asp Ser Thr
            180                 185                 190

Tyr Tyr Ala Asp Ser Val Lys Gly Arg Phe Thr Ile Ser Arg Asp Asn
        195                 200                 205

Ala Lys Asn Thr Met Tyr Leu Gln Met Asn Ser Leu Lys Pro Glu Asp
    210                 215                 220

Thr Ala Val Tyr Tyr Cys Asn Ala Asn Ser Glu Tyr Gly Asp Ser Tyr
225                 230                 235                 240

Trp Gly Gln Gly Thr Gln Val Thr Val Ser Ser Lys Lys Lys His His
                245                 250                 255

His His His His
        260

<210> SEQ ID NO 19
<211> LENGTH: 9
<212> TYPE: PRT
<213> ORGANISM: artificial sequence
<220> FEATURE:
<223> OTHER INFORMATION: CDR

<400> SEQUENCE: 19

Arg Thr Phe Asn Thr Tyr Gly Met Gly
1               5

<210> SEQ ID NO 20
<211> LENGTH: 17
<212> TYPE: PRT
<213> ORGANISM: artificial sequence
<220> FEATURE:
<223> OTHER INFORMATION: CDR

<400> SEQUENCE: 20

Thr Ile Ser Trp Ser Gly Asp Ser Thr Tyr Tyr Ala Asp Ser Val Lys
1               5                   10                  15

Gly

<210> SEQ ID NO 21
<211> LENGTH: 8
<212> TYPE: PRT
<213> ORGANISM: artificial sequence
<220> FEATURE:
<223> OTHER INFORMATION: CDR

<400> SEQUENCE: 21

Asn Ser Glu Tyr Gly Asp Ser Tyr
1               5

<210> SEQ ID NO 22
<211> LENGTH: 9
<212> TYPE: PRT
<213> ORGANISM: artificial sequence
<220> FEATURE:
<223> OTHER INFORMATION: CDR

<400> SEQUENCE: 22

Phe Ile Phe Asn Thr Tyr Ser Met Arg
1               5

<210> SEQ ID NO 23
<211> LENGTH: 16
<212> TYPE: PRT
<213> ORGANISM: artificial sequence
```

```
<220> FEATURE:
<223> OTHER INFORMATION: CDR

<400> SEQUENCE: 23

Ser Ile Ser Thr Gly Gly Tyr Ser Thr Tyr Ala Asp Ser Val Lys Gly
1               5                   10                  15

<210> SEQ ID NO 24
<211> LENGTH: 9
<212> TYPE: PRT
<213> ORGANISM: artificial sequence
<220> FEATURE:
<223> OTHER INFORMATION: CDR

<400> SEQUENCE: 24

Gly Ala Phe Val Arg Gly Glu Arg Pro
1               5

<210> SEQ ID NO 25
<211> LENGTH: 9
<212> TYPE: PRT
<213> ORGANISM: artificial sequence
<220> FEATURE:
<223> OTHER INFORMATION: CDR

<400> SEQUENCE: 25

Ser Ile Phe Ser Ile Ala Ser Met Gly
1               5

<210> SEQ ID NO 26
<211> LENGTH: 16
<212> TYPE: PRT
<213> ORGANISM: artificial sequence
<220> FEATURE:
<223> OTHER INFORMATION: CDR

<400> SEQUENCE: 26

Thr Ile Thr Ser Asp Gly Ser Thr Lys Tyr Ala Asp Ser Val Lys Gly
1               5                   10                  15

<210> SEQ ID NO 27
<211> LENGTH: 14
<212> TYPE: PRT
<213> ORGANISM: artificial sequence
<220> FEATURE:
<223> OTHER INFORMATION: CDR

<400> SEQUENCE: 27

Asp Ala Asp Asp Leu Glu Pro Gly Ser Tyr Tyr Tyr Asp Tyr
1               5                   10

<210> SEQ ID NO 28
<211> LENGTH: 9
<212> TYPE: PRT
<213> ORGANISM: artificial sequence
<220> FEATURE:
<223> OTHER INFORMATION: CDR

<400> SEQUENCE: 28

Ser Ile Phe Ser Ile Tyr Val Met Ala
1               5

<210> SEQ ID NO 29
<211> LENGTH: 16
<212> TYPE: PRT
<213> ORGANISM: artificial sequence
<220> FEATURE:
```

<223> OTHER INFORMATION: CDR

<400> SEQUENCE: 29

Thr Val Thr Ser Gly Gly Ala Thr Asn Tyr Ala Asn Ser Val Lys Gly
1               5                   10                  15

<210> SEQ ID NO 30
<211> LENGTH: 14
<212> TYPE: PRT
<213> ORGANISM: artificial sequence
<220> FEATURE:
<223> OTHER INFORMATION: CDR

<400> SEQUENCE: 30

Glu Asp Tyr Tyr Asp Tyr Gly Leu Ser Arg Ser Lys Ile Tyr
1               5                   10

<210> SEQ ID NO 31
<211> LENGTH: 9
<212> TYPE: PRT
<213> ORGANISM: artificial sequence
<220> FEATURE:
<223> OTHER INFORMATION: CDR

<400> SEQUENCE: 31

Ser Ile Ser Glu Ile Asp Ala Met Tyr
1               5

<210> SEQ ID NO 32
<211> LENGTH: 16
<212> TYPE: PRT
<213> ORGANISM: artificial sequence
<220> FEATURE:
<223> OTHER INFORMATION: CDR

<400> SEQUENCE: 32

Gly Ile Thr Asn Asp Gly Thr Arg Tyr Tyr Ala Asp Ser Val Lys Gly
1               5                   10                  15

<210> SEQ ID NO 33
<211> LENGTH: 8
<212> TYPE: PRT
<213> ORGANISM: artificial sequence
<220> FEATURE:
<223> OTHER INFORMATION: CDR

<400> SEQUENCE: 33

Leu Pro Asn Pro Pro Pro Gly Tyr
1               5

<210> SEQ ID NO 34
<211> LENGTH: 9
<212> TYPE: PRT
<213> ORGANISM: artificial sequence
<220> FEATURE:
<223> OTHER INFORMATION: CDR

<400> SEQUENCE: 34

Phe Thr Ile Ser Asn Tyr Pro Met Thr
1               5

<210> SEQ ID NO 35
<211> LENGTH: 17
<212> TYPE: PRT
<213> ORGANISM: artificial sequence
<220> FEATURE:
<223> OTHER INFORMATION: CDR

```
<400> SEQUENCE: 35

Arg Ile Asn Ser Gly Gly Asp Arg Thr Leu Tyr Ala Asp Ser Val Lys
1               5                   10                  15

Gly

<210> SEQ ID NO 36
<211> LENGTH: 7
<212> TYPE: PRT
<213> ORGANISM: artificial sequence
<220> FEATURE:
<223> OTHER INFORMATION: CDR

<400> SEQUENCE: 36

Ser Gly Ala Gly Trp Arg Tyr
1               5

<210> SEQ ID NO 37
<211> LENGTH: 9
<212> TYPE: PRT
<213> ORGANISM: artificial sequence
<220> FEATURE:
<223> OTHER INFORMATION: CDR

<400> SEQUENCE: 37

Ser Ile Ser Asp Ile Asp Ala Met Tyr
1               5

<210> SEQ ID NO 38
<211> LENGTH: 16
<212> TYPE: PRT
<213> ORGANISM: artificial sequence
<220> FEATURE:
<223> OTHER INFORMATION: CDR

<400> SEQUENCE: 38

Gly Ile Thr Asn Asp Gly Thr Glu Tyr Phe Ala Asp Ser Val Lys Gly
1               5                   10                  15

<210> SEQ ID NO 39
<211> LENGTH: 8
<212> TYPE: PRT
<213> ORGANISM: artificial sequence
<220> FEATURE:
<223> OTHER INFORMATION: CDR

<400> SEQUENCE: 39

Leu Pro Asn Pro Pro Pro Gly Tyr
1               5

<210> SEQ ID NO 40
<211> LENGTH: 9
<212> TYPE: PRT
<213> ORGANISM: artificial sequence
<220> FEATURE:
<223> OTHER INFORMATION: CDR

<400> SEQUENCE: 40

Arg Thr Phe Asn Thr Tyr Gly Met Gly
1               5

<210> SEQ ID NO 41
<211> LENGTH: 17
<212> TYPE: PRT
<213> ORGANISM: artificial sequence
<220> FEATURE:
```

<223> OTHER INFORMATION: CDR

<400> SEQUENCE: 41

Thr Ile Ser Trp Ser Gly Asp Ser Thr Tyr Tyr Ala Asp Ser Val Lys
1               5                   10                  15
Gly

<210> SEQ ID NO 42
<211> LENGTH: 8
<212> TYPE: PRT
<213> ORGANISM: artificial sequence
<220> FEATURE:
<223> OTHER INFORMATION: CDR

<400> SEQUENCE: 42

Asn Ser Glu Tyr Gly Asp Ser Tyr
1               5

<210> SEQ ID NO 43
<211> LENGTH: 9
<212> TYPE: PRT
<213> ORGANISM: artificial sequence
<220> FEATURE:
<223> OTHER INFORMATION: CDR

<400> SEQUENCE: 43

Phe Thr Ile Ser Asn Tyr Pro Met Thr
1               5

<210> SEQ ID NO 44
<211> LENGTH: 17
<212> TYPE: PRT
<213> ORGANISM: artificial sequence
<220> FEATURE:
<223> OTHER INFORMATION: CDR

<400> SEQUENCE: 44

Arg Ile Asn Ser Gly Gly Asp Arg Thr Leu Tyr Ala Asp Ser Val Lys
1               5                   10                  15
Gly

<210> SEQ ID NO 45
<211> LENGTH: 7
<212> TYPE: PRT
<213> ORGANISM: artificial sequence
<220> FEATURE:
<223> OTHER INFORMATION: CDR

<400> SEQUENCE: 45

Ser Gly Ala Gly Trp Arg Tyr
1               5

<210> SEQ ID NO 46
<211> LENGTH: 9
<212> TYPE: PRT
<213> ORGANISM: artificial sequence
<220> FEATURE:
<223> OTHER INFORMATION: CDR

<400> SEQUENCE: 46

Phe Thr Ile Ser Asn Tyr Pro Met Thr
1               5

<210> SEQ ID NO 47
<211> LENGTH: 17

```
<212> TYPE: PRT
<213> ORGANISM: artificial sequence
<220> FEATURE:
<223> OTHER INFORMATION: CDR

<400> SEQUENCE: 47

Arg Ile Asn Ser Gly Gly Asp Arg Thr Leu Tyr Ala Asp Ser Val Lys
1               5                   10                  15

Gly

<210> SEQ ID NO 48
<211> LENGTH: 7
<212> TYPE: PRT
<213> ORGANISM: artificial sequence
<220> FEATURE:
<223> OTHER INFORMATION: CDR

<400> SEQUENCE: 48

Ser Gly Ala Gly Trp Arg Tyr
1               5

<210> SEQ ID NO 49
<211> LENGTH: 9
<212> TYPE: PRT
<213> ORGANISM: artificial sequence
<220> FEATURE:
<223> OTHER INFORMATION: CDR

<400> SEQUENCE: 49

Arg Thr Phe Asn Thr Tyr Gly Met Gly
1               5

<210> SEQ ID NO 50
<211> LENGTH: 17
<212> TYPE: PRT
<213> ORGANISM: artificial sequence
<220> FEATURE:
<223> OTHER INFORMATION: CDR

<400> SEQUENCE: 50

Thr Ile Ser Trp Ser Gly Asp Ser Thr Tyr Tyr Ala Asp Ser Val Lys
1               5                   10                  15

Gly

<210> SEQ ID NO 51
<211> LENGTH: 8
<212> TYPE: PRT
<213> ORGANISM: artificial sequence
<220> FEATURE:
<223> OTHER INFORMATION: CDR

<400> SEQUENCE: 51

Asn Ser Glu Tyr Gly Asp Ser Tyr
1               5
```